US012590167B2

(12) United States Patent
Adrian et al.

(10) Patent No.: US 12,590,167 B2
(45) Date of Patent: Mar. 31, 2026

(54) COMBINATION THERAPIES AGAINST CANCER TARGETING CD38 AND TGF-β

(71) Applicant: SANOFI, Paris (FR)

(72) Inventors: Francisco Adrian, Belmont, MA (US); Richard C. Gregory, Framingham, MA (US); Gary Shapiro, Arlington, MA (US); Helgi Van De Velde, Retie (BE)

(73) Assignee: Sanofi, Paris (FR)

( * ) Notice: Subject to any disclaimer, the term of this patent is extended or adjusted under 35 U.S.C. 154(b) by 1432 days.

(21) Appl. No.: 17/259,135

(22) PCT Filed: Jul. 10, 2019

(86) PCT No.: PCT/IB2019/055885

§ 371 (c)(1),
(2) Date: Jan. 8, 2021

(87) PCT Pub. No.: WO2020/012383

PCT Pub. Date: Jan. 16, 2020

(65) Prior Publication Data

US 2021/0155708 A1     May 27, 2021

Related U.S. Application Data

(60) Provisional application No. 62/696,198, filed on Jul. 10, 2018.

(30) Foreign Application Priority Data

Apr. 11, 2019     (EP) ..................................... 19305470

(51) Int. Cl.
| | |
|---|---|
| C07K 16/28 | (2006.01) |
| A61K 31/12 | (2006.01) |
| A61K 31/573 | (2006.01) |
| A61K 39/00 | (2006.01) |
| A61P 35/00 | (2006.01) |
| C07K 16/22 | (2006.01) |

(52) U.S. Cl.
CPC .......... C07K 16/2896 (2013.01); C07K 16/22 (2013.01); A61K 31/12 (2013.01); A61K 2039/507 (2013.01); C07K 2317/565 (2013.01)

(58) Field of Classification Search
CPC ............... C07K 16/2896; C07K 16/22; C07K 2317/565; C07K 2317/732; C07K 2317/76; A61K 31/12; A61K 2039/507; A61K 31/573; A61P 35/00
See application file for complete search history.

(56) References Cited

U.S. PATENT DOCUMENTS

| | | | |
|---|---|---|---|
| 7,527,791 B2 | 5/2009 | Adams et al. | |
| 7,723,486 B2 | 5/2010 | Ledbetter et al. | |
| 8,153,765 B2 * | 4/2012 | Park ........................ | A61P 35/00 |
| | | | 530/389.7 |
| 8,569,462 B2 | 10/2013 | Bedinger et al. | |
| 9,314,522 B2 * | 4/2016 | Deckert ............. | A61K 39/3955 |
| 10,342,869 B2 * | 7/2019 | Hann ...................... | A61K 31/37 |
| 10,766,955 B2 * | 9/2020 | Shapiro ............. | C07K 16/2818 |
| 11,242,384 B2 * | 2/2022 | Shapiro ................. | C07K 16/32 |
| 2006/0251658 A1 * | 11/2006 | Ledbetter ............... | C07K 16/22 |
| | | | 536/23.53 |
| 2010/0254985 A1 | 10/2010 | Allan et al. | |
| 2014/0248238 A1 * | 9/2014 | Wilson, Jr. .............. | A61P 35/00 |
| | | | 424/85.5 |
| 2017/0066821 A1 | 3/2017 | Ledbetter et al. | |
| 2018/0208650 A1 * | 7/2018 | Qiu ........................ | A61P 35/04 |
| 2018/0289771 A1 | 10/2018 | Shan et al. | |
| 2021/0171650 A1 * | 6/2021 | Audat .................. | A61K 31/454 |
| 2021/0188996 A1 * | 6/2021 | Huille ..................... | A61P 35/00 |
| 2022/0195026 A1 * | 6/2022 | Shapiro ................. | C07K 16/30 |

FOREIGN PATENT DOCUMENTS

| | | | | |
|---|---|---|---|---|
| WO | WO 2006/086469 A2 | 8/2006 | | |
| WO | WO 2007/008463 A2 | 1/2007 | | |
| WO | WO 2014/153435 A1 | 9/2014 | | |
| WO | WO-2014159911 A1 * | 10/2014 | ........... | A61K 31/336 |
| WO | WO 2015/066450 A1 | 5/2015 | | |
| WO | WO 2016/125169 A1 | 8/2016 | | |
| WO | WO 2018/130928 A1 | 7/2018 | | |
| WO | WO 2018/134681 A1 | 7/2018 | | |
| WO | WO 2020/146795 A1 | 7/2020 | | |

OTHER PUBLICATIONS

NCI Thesaurus. "Isatuximab (Code C90578)". Accessed on Apr. 13, 2024 from: https://ncit.nci.nih.gov/ncitbrowser/ConceptReport.jsp? dictionary=NCI%20Thesaurus&code=C90578 . Archived (Way Back Machine): Sep. 21, 2015. https://web.archive.org/web/ 20240000000000*/https://ncit.nci.nih.gov (Year: 2015).*
Mahaweni et al. Cancer Immunology, Immunotherapy, Mar. 2, 2018, XP036502818; cited on the Written Opinion of the Int. Search Authority for PCT/IB2019/055885 (Year: 2018).*
CDER. "BLA Multi-disciplinary Review and Evaluation BLA 761113 Sarclisa (isatuximab)", published Feb. 1, 2016. (Year: 2016).*
Jeffry et al. BONE, 2016, XP029695211; cited on the Written Opinion of the Int. Search Authority for PCT/IB2019/055885 (Year: 2016).*
Trotta et al. TGF-beta utilizes SMAD3 to inhibit CD16-mediated IFN-gamma production and antibody-dependent cellular cytotoxicity in human NK cells. J Immunol. Sep. 15, 2008;181(6):3784-92. (Year: 2008) (Year: 2008).*

(Continued)

*Primary Examiner* — Mark Halvorson
*Assistant Examiner* — Lea S O'Brien
(74) *Attorney, Agent, or Firm* — Steptoe LLP; Z. Ying Li; Mauricio Alvarez

(57) ABSTRACT

The present disclosure relates to combination cancer therapies targeting CD38 and TGF-β using antibodies specific for these targets. Also provided are compositions useful in the therapies.

11 Claims, 8 Drawing Sheets

Specification includes a Sequence Listing.

(56)             References Cited

OTHER PUBLICATIONS

Watanabe et al. NK cell dysfunction with down-regulated CD16 and up-regulated CD56 molecules in patients with esophageal squamous cell carcinoma, Diseases of the Esophagus, vol. 23, Issue 8, Nov. 1, 2010, pp. 675-681. (Year: 2010).*

Urashima, Mitsuyoshi, et al. "Transforming growth factor-beta1: differential effects on multiple myeloma versus normal B cells." (1996): 1928-1938. (Year: 1999).*

Richardson, Paul G., et al. "Isatuximab plus pomalidomide/dexamethasone versus pomalidomide/dexamethasone in relapsed/refractory multiple myeloma: ICARIA Phase III study design." Future Oncology 14.11 (2017): 1035-1047. (Year: 2017).*

Tamura, Hideto. "Immunopathogenesis and immunotherapy of multiple myeloma." International journal of hematology 107.3 (Jan. 2018): 278-285. (Year: 2018).*

Rouce, R., Shaim, H., Sekine, T. et al. The TGF-β/SMAD pathway is an important mechanism for NK cell immune evasion in childhood B-acute lymphoblastic leukemia. Leukemia 30, 800-811 (2016). (Year: 2016).*

Shen et al., "Isatuximab in the Treatment of Multiple Myeloma: A Review and Comparison With Daratumumab", Technol Cancer Res Treat., (2022) vol. 21, XP093157542 (9 pages).

Akhurst et al., "Targeting the TGFbeta; signalling pathway in disease," Nature Reviews Drug Discovery (2012) 11(10):1474-76.

Almagro & Fransson, "Humanization of antibodies," Front Biosci. (2008) 13:1619-33.

Angal et al., "A Single Amino Acid Substitution Abolishes the Heterogeneity of Chimeric Mouse/Human (IgG4) Antibody," Mol Immunol (1993) 30(1):105-8.

Bloom et al., "Intrachain disulfide bond in the core hinge region of human IgG4," Protein Science (1997) 6:407-15.

Burks et al., "In vitro scanning saturation mutagenesis of an antibody binding pocket," Proc Natl Acad Sci USA, (1997) 94:412-17.

Chothia & Lesk, "Canonical Structures for the Hypervariable Regions of Immunoglobulins," J. Mol. Biol. (1987) 196:901-17.

Chothia et al., "Conformations of immunoglobulin hypervariable regions," Nature (1989) 342:878-83.

Feng et al., "Suppresses Induction and Function of T Regulatory Cells to Mitigate Immunosuppression in Multiple Myeloma11," Clin. Cancer Res. (2017) 23(15):4290-300.

Kubiczkova et al., "TGF-β—an excellent servant but a bad master" J Transl Med. (2012) 10(183):1-24.

Lefranc et al., "IMGT unique numbering for immunoglobulin and T cell receptor variable domains and Ig superfamily V-like domains," Dev Comp Immunol (2003) 27(1):55-77.

Magdelaine-Beuzelin et al., "Structure-function relationships of the variable domains of monoclonal antibodies approved for cancer treatment," Crit Rev.Oncol Hematol. (2007) 64:210-25.

Mahaweni et al., Daratumumab augments alloreactive natural killer cell cytotoxicity towards CD38+ multiple myeloma cell lines in a biochemical context mimicking tumour microenvironment conditions, Cancer Immunology (2018) 67(6):861-72.

Matsumoto et al., "TGF-β-related mechanisms of bone destruction in multiple myeloma" Bone (2011) 48(1):129-34.

Morandi et al., "CD38: A Target for Immunotherapeutic Approaches in Multiple Myeloma," Front Immunol. (2018) 9:2722.

Morris et al., "Phase I Study of GC1008 (Fresolimumab): A Human Anti-Transforming Growth Factor-Beta (TGF&bgr;) Monoclonal Antibody in Patients with Advanced Malignant Melanoma or Renal Cell Carcinoma," PLOS One (2014) 9(3):e90353.

Nyman et al., "Combined treatment with a transforming growth factor beta inhibitor (1D11) and bortezomib improves bone architecture in a mouse model of myeloma-induced bone disease", Bone, Pergamon Press., Oxford, GB, (2016) vol. 91.

Pereira et al., "Tgfβ-Imprinting Decrease CD38 Expression and Lead to Metabolic Reprogramming on Primary NK Cell," Blood (2020) 136(Supplement 1):4.

Schuurman et al., "The inter-heavy chain disulfide bonds of IgG4 are in equilibrium with intra-chain disulfide bonds," Mol. Immunol (2001) 38(1):1-8.

Salas-Solanos et al., "Optimization and Validation of a Quantitative Capillary Electrophoresis Sodium Dodecyl Sulfate Method for Quality Control and Stability Monitoring of Monoclonal Antibodies," Anal Chem. (2006) 78:6583-94.

Tol J. et al., "Chemotherapy, Bevacizumab, and Cetuximab in Metastatic Colorectal Cancer," N Engl J Med. (2009) 360:563-72.

Wang et al., "The role of the CD95, CD38 and TGFbeta1 during active human cytomegalovirus infection in liver transplantation," Cytokine. (2006) 35(3-4):193-9.

Wu et al., "Stepwise in vitro affinity maturation of Vitaxin, an alphav beta3-specific humanized mAb," Proc Natl Acad Sci USA (1998) 95:6037-42.

* cited by examiner

FIG. 4

TGFβ Inhibits Ab2-Mediated ADCC

Norm. ADCC (+/-SEM)

100    50    0

Untreated    0.1ng/mL    1ng/mL    10ng/mL

TGFβ Treatment

NK cytolytic activity
NK:K562(4:1)

SEQUENCE LISTING

<160> NUMBER OF SEQ ID NOS: 44

<210> SEQ ID NO 1
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Asn
            20                  25                  30

Val Ile Ser Trp Val Arg Gln Ala Pro Gly Gln Gly Leu Glu Trp Met
        35                  40                  45

Gly Gly Val Ile Pro Ile Val Asp Ile Ala Asn Tyr Ala Gln Arg Phe
    50                  55                  60

Lys Gly Arg Val Thr Ile Thr Ala Asp Glu Ser Thr Ser Thr Thr Tyr
65                  70                  75                  80

Met Glu Leu Ser Ser Leu Arg Ser Glu Asp Thr Ala Val Tyr Tyr Cys
                85                  90                  95

Ala Ser Thr Leu Gly Leu Val Leu Asp Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350
```

-continued

```
Pro Ser Gln Glu Glu Met Thr Lys Asn Gln Val Ser Leu Thr Cys Leu
        355             360             365

Val Lys Gly Phe Tyr Pro Ser Asp Ile Ala Val Glu Trp Glu Ser Asn
        370             375             380

Gly Gln Pro Glu Asn Asn Tyr Lys Thr Thr Pro Pro Val Leu Asp Ser
385             390             395             400

Asp Gly Ser Phe Phe Leu Tyr Ser Arg Leu Thr Val Asp Lys Ser Arg
            405             410             415

Trp Gln Glu Gly Asn Val Phe Ser Cys Ser Val Met His Glu Ala Leu
        420             425             430

His Asn His Tyr Thr Gln Lys Ser Leu Ser Leu Ser Leu Gly Lys
        435             440             445
```

```
<210> SEQ ID NO 2
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2
```

```
Glu Thr Val Leu Thr Gln Ser Pro Gly Thr Leu Ser Leu Ser Pro Gly
1               5               10              15

Glu Arg Ala Thr Leu Ser Cys Arg Ala Ser Gln Ser Leu Gly Ser Ser
        20              25              30

Tyr Leu Ala Trp Tyr Gln Gln Lys Pro Gly Gln Ala Pro Arg Leu Leu
        35              40              45

Ile Tyr Gly Ala Ser Ser Arg Ala Pro Gly Ile Pro Asp Arg Phe Ser
        50              55              60

Gly Ser Gly Ser Gly Thr Asp Phe Thr Leu Thr Ile Ser Arg Leu Glu
65              70              75              80

Pro Glu Asp Phe Ala Val Tyr Tyr Cys Gln Gln Tyr Ala Asp Ser Pro
            85              90              95

Ile Thr Phe Gly Gln Gly Thr Arg Leu Glu Ile Lys Arg Thr Val Ala
        100             105             110

Ala Pro Ser Val Phe Ile Phe Pro Pro Ser Asp Glu Gln Leu Lys Ser
        115             120             125

Gly Thr Ala Ser Val Val Cys Leu Leu Asn Asn Phe Tyr Pro Arg Glu
        130             135             140

Ala Lys Val Gln Trp Lys Val Asp Asn Ala Leu Gln Ser Gly Asn Ser
145             150             155             160

Gln Glu Ser Val Thr Glu Gln Asp Ser Lys Asp Ser Thr Tyr Ser Leu
            165             170             175

Ser Ser Thr Leu Thr Leu Ser Lys Ala Asp Tyr Glu Lys His Lys Val
            180             185             190

Tyr Ala Cys Glu Val Thr His Gln Gly Leu Ser Ser Pro Val Thr Lys
        195             200             205

Ser Phe Asn Arg Gly Glu Cys
    210             215
```

```
<210> SEQ ID NO 3
<211> LENGTH: 120
<212> TYPE: PRT
<213> ORGANISM: Artificial Sequence
<220> FEATURE:
```

<221> NAME/KEY: source
<223> OTHER INFORMATION: /note="Description of Artificial Sequence:
      Synthetic polypeptide"

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Asn
            20                  25                  30

Val Ile Ser Trp Val Arg Gln Ala Pro Gly Gln Gly Leu Glu Trp Met
        35                  40                  45

Gly Gly Val Ile Pro Ile Val Asp Ile Ala Asn Tyr Ala Gln Arg Phe
    50                  55                  60

Lys Gly Arg Val Thr Ile Thr Ala Asp Glu Ser Thr Ser Thr Thr Tyr
65                  70                  75                  80

Met Glu Leu Ser Ser Leu Arg Ser Glu Asp Thr Ala Val Tyr Tyr Cys
                85                  90                  95

Ala Ser Thr Leu Gly Leu Val Leu Asp Ala Met Asp Tyr Trp Gly Gln
            100                 105                 110

Gly Thr Leu Val Thr Val Ser Ser
        115                 120

<210> SEQ ID NO 4
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Glu Thr Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Asp Ser Pro
                85                  90                  95

Ile Thr Phe Gly Gln Gly Thr Arg Leu Glu Ile Lys
            100                 105

<210> SEQ ID NO 5
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Ser Asn Val Ile Ser
1               5

-continued

```
<210> SEQ ID NO 6
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gly Val Ile Pro Ile Val Asp Ile Ala Asn Tyr
1               5                   10

<210> SEQ ID NO 7
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Thr Leu Gly Leu Val Leu Asp Ala Met Asp Tyr
1               5                   10

<210> SEQ ID NO 8
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Arg Ala Ser Gln Ser Leu Gly Ser Ser Tyr Leu Ala
1               5                   10

<210> SEQ ID NO 9
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Gly Ala Ser Ser Arg Ala Pro
1               5

<210> SEQ ID NO 10
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Gln Gln Tyr Ala Asp Ser Pro Ile Thr
1               5

<210> SEQ ID NO 11
<211> LENGTH: 450
<212> TYPE: PRT
<213> ORGANISM: Artificial Sequence
```

-continued

```
<220> FEATURE:
<221> NAME/KEY: source
<223> OTHER INFORMATION: /note="Description of Artificial Sequence:
      Synthetic polypeptide"

<400> SEQUENCE: 11

Gln Val Gln Leu Val Gln Ser Gly Ala Glu Val Ala Lys Pro Gly Thr
1               5                   10                  15

Ser Val Lys Leu Ser Cys Lys Ala Ser Gly Tyr Thr Phe Thr Asp Tyr
            20                  25                  30

Trp Met Gln Trp Val Lys Gln Arg Pro Gly Gln Gly Leu Glu Trp Ile
        35                  40                  45

Gly Thr Ile Tyr Pro Gly Asp Gly Asp Thr Gly Tyr Ala Gln Lys Phe
    50                  55                  60

Gln Gly Lys Ala Thr Leu Thr Ala Asp Lys Ser Ser Lys Thr Val Tyr
65                  70                  75                  80

Met His Leu Ser Ser Leu Ala Ser Glu Asp Ser Ala Val Tyr Tyr Cys
                85                  90                  95

Ala Arg Gly Asp Tyr Tyr Gly Ser Asn Ser Leu Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380
```

-continued

```
Glu Ser Asn Gly Gln Pro Glu Asn Asn Tyr Lys Thr Thr Pro Pro Val
385             390             395             400

Leu Asp Ser Asp Gly Ser Phe Phe Leu Tyr Ser Lys Leu Thr Val Asp
                405             410             415

Lys Ser Arg Trp Gln Gln Gly Asn Val Phe Ser Cys Ser Val Met His
            420             425             430

Glu Ala Leu His Asn His Tyr Thr Gln Lys Ser Leu Ser Leu Ser Pro
        435             440             445

Gly Lys
    450
```

```
<210> SEQ ID NO 12
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Asp Ile Val Met Thr Gln Ser His Leu Ser Met Ser Thr Ser Leu Gly
1               5               10              15

Asp Pro Val Ser Ile Thr Cys Lys Ala Ser Gln Asp Val Ser Thr Val
            20              25              30

Val Ala Trp Tyr Gln Gln Lys Pro Gly Gln Ser Pro Arg Arg Leu Ile
            35              40              45

Tyr Ser Ala Ser Tyr Arg Tyr Ile Gly Val Pro Asp Arg Phe Thr Gly
        50              55              60

Ser Gly Ala Gly Thr Asp Phe Thr Phe Thr Ile Ser Ser Val Gln Ala
65              70              75              80

Glu Asp Leu Ala Val Tyr Tyr Cys Gln Gln His Tyr Ser Pro Pro Tyr
            85              90              95

Thr Phe Gly Gly Gly Thr Lys Leu Glu Ile Lys Arg Thr Val Ala Ala
            100             105             110

Pro Ser Val Phe Ile Phe Pro Pro Ser Asp Glu Gln Leu Lys Ser Gly
            115             120             125

Thr Ala Ser Val Val Cys Leu Leu Asn Asn Phe Tyr Pro Arg Glu Ala
        130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
            165             170             175

Ser Thr Leu Thr Leu Ser Lys Ala Asp Tyr Glu Lys His Lys Val Tyr
            180             185             190

Ala Cys Glu Val Thr His Gln Gly Leu Ser Ser Pro Val Thr Lys Ser
            195             200             205

Phe Asn Arg Gly Glu Cys
    210
```

```
<210> SEQ ID NO 13
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 13

Gln Val Gln Leu Val Gln Ser Gly Ala Glu Val Ala Lys Pro Gly Thr
1               5                   10                  15

Ser Val Lys Leu Ser Cys Lys Ala Ser Gly Tyr Thr Phe Thr Asp Tyr
            20                  25                  30

Trp Met Gln Trp Val Lys Gln Arg Pro Gly Gln Gly Leu Glu Trp Ile
        35                  40                  45

Gly Thr Ile Tyr Pro Gly Asp Gly Asp Thr Gly Tyr Ala Gln Lys Phe
    50                  55                  60

Gln Gly Lys Ala Thr Leu Thr Ala Asp Lys Ser Ser Lys Thr Val Tyr
65                  70                  75                  80

Met His Leu Ser Ser Leu Ala Ser Glu Asp Ser Ala Val Tyr Tyr Cys
            85                  90                  95

Ala Arg Gly Asp Tyr Tyr Gly Ser Asn Ser Leu Asp Tyr Trp Gly Gln
            100                 105                 110

Gly Thr Ser Val Thr Val Ser Ser
        115                 120

<210> SEQ ID NO 14
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Asp Ile Val Met Thr Gln Ser His Leu Ser Met Ser Thr Ser Leu Gly
1               5                   10                  15

Asp Pro Val Ser Ile Thr Cys Lys Ala Ser Gln Asp Val Ser Thr Val
            20                  25                  30

Val Ala Trp Tyr Gln Gln Lys Pro Gly Gln Ser Pro Arg Arg Leu Ile
        35                  40                  45

Tyr Ser Ala Ser Tyr Arg Tyr Ile Gly Val Pro Asp Arg Phe Thr Gly
    50                  55                  60

Ser Gly Ala Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Pro Pro Tyr
            85                  90                  95

Thr Phe Gly Gly Gly Thr Lys Leu Glu Ile Lys
            100                 105

<210> SEQ ID NO 15
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Asp Tyr Trp Met Gln
1               5

<210> SEQ ID NO 16
<211> LENGTH: 17
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 16

Thr Ile Tyr Pro Gly Asp Gly Asp Thr Gly Tyr Ala Gln Lys Phe Gln
1               5                   10                  15

Gly

<210> SEQ ID NO 17
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Gly Asp Tyr Tyr Gly Ser Asn Ser Leu Asp Tyr
1               5                   10

<210> SEQ ID NO 18
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Lys Ala Ser Gln Asp Val Ser Thr Val Val Ala
1               5                   10

<210> SEQ ID NO 19
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Ser Ala Ser Tyr Arg Tyr Ile
1               5

<210> SEQ ID NO 20
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Gln Gln His Tyr Ser Pro Pro Tyr Thr
1               5

<210> SEQ ID NO 21
<211> LENGTH: 390
<212> TYPE: PRT
<213> ORGANISM: Homo sapiens

<400> SEQUENCE: 21
```

-continued

```
Met Pro Pro Ser Gly Leu Arg Leu Leu Leu Leu Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
            115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
            195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
            245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
    275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
            325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
            355                 360                 365

Tyr Val Gly Arg Lys Pro Lys Val Glu Gln Leu Ser Asn Met Ile Val
    370                 375                 380

Arg Ser Cys Lys Cys Ser
385                 390
```

<210> SEQ ID NO 22
<211> LENGTH: 414

-continued

```
<212> TYPE: PRT
<213> ORGANISM: Homo sapiens

<400> SEQUENCE: 22

Met His Tyr Cys Val Leu Ser Ala Phe Leu Ile Leu His Leu Val Thr
1               5                   10                  15

Val Ala Leu Ser Leu Ser Thr Cys Ser Thr Leu Asp Met Asp Gln Phe
            20                  25                  30

Met Arg Lys Arg Ile Glu Ala Ile Arg Gly Gln Ile Leu Ser Lys Leu
        35                  40                  45

Lys Leu Thr Ser Pro Pro Glu Asp Tyr Pro Glu Pro Glu Glu Val Pro
    50                  55                  60

Pro Glu Val Ile Ser Ile Tyr Asn Ser Thr Arg Asp Leu Leu Gln Glu
65                  70                  75                  80

Lys Ala Ser Arg Arg Ala Ala Ala Cys Glu Arg Glu Arg Ser Asp Glu
                85                  90                  95

Glu Tyr Tyr Ala Lys Glu Val Tyr Lys Ile Asp Met Pro Pro Phe Phe
            100                 105                 110

Pro Ser Glu Asn Ala Ile Pro Pro Thr Phe Tyr Arg Pro Tyr Phe Arg
            115                 120                 125

Ile Val Arg Phe Asp Val Ser Ala Met Glu Lys Asn Ala Ser Asn Leu
    130                 135                 140

Val Lys Ala Glu Phe Arg Val Phe Arg Leu Gln Asn Pro Lys Ala Arg
145                 150                 155                 160

Val Pro Glu Gln Arg Ile Glu Leu Tyr Gln Ile Leu Lys Ser Lys Asp
                165                 170                 175

Leu Thr Ser Pro Thr Gln Arg Tyr Ile Asp Ser Lys Val Val Lys Thr
            180                 185                 190

Arg Ala Glu Gly Glu Trp Leu Ser Phe Asp Val Thr Asp Ala Val His
            195                 200                 205

Glu Trp Leu His His Lys Asp Arg Asn Leu Gly Phe Lys Ile Ser Leu
    210                 215                 220

His Cys Pro Cys Cys Thr Phe Val Pro Ser Asn Asn Tyr Ile Ile Pro
225                 230                 235                 240

Asn Lys Ser Glu Glu Leu Glu Ala Arg Phe Ala Gly Ile Asp Gly Thr
                245                 250                 255

Ser Thr Tyr Thr Ser Gly Asp Gln Lys Thr Ile Lys Ser Thr Arg Lys
            260                 265                 270

Lys Asn Ser Gly Lys Thr Pro His Leu Leu Leu Met Leu Leu Pro Ser
            275                 280                 285

Tyr Arg Leu Glu Ser Gln Gln Thr Asn Arg Arg Lys Lys Arg Ala Leu
    290                 295                 300

Asp Ala Ala Tyr Cys Phe Arg Asn Val Gln Asp Asn Cys Cys Leu Arg
305                 310                 315                 320

Pro Leu Tyr Ile Asp Phe Lys Arg Asp Leu Gly Trp Lys Trp Ile His
                325                 330                 335

Glu Pro Lys Gly Tyr Asn Ala Asn Phe Cys Ala Gly Ala Cys Pro Tyr
            340                 345                 350

Leu Trp Ser Ser Asp Thr Gln His Ser Arg Val Leu Ser Leu Tyr Asn
            355                 360                 365

Thr Ile Asn Pro Glu Ala Ser Ala Ser Pro Cys Cys Val Ser Gln Asp
    370                 375                 380

Leu Glu Pro Leu Thr Ile Leu Tyr Tyr Ile Gly Lys Thr Pro Lys Ile
385                 390                 395                 400
```

-continued

```
Glu Gln Leu Ser Asn Met Ile Val Lys Ser Cys Lys Cys Ser
            405                 410

<210> SEQ ID NO 23
<211> LENGTH: 412
<212> TYPE: PRT
<213> ORGANISM: Homo sapiens

<400> SEQUENCE: 23

Met Lys Met His Leu Gln Arg Ala Leu Val Val Leu Ala Leu Leu Asn
1               5                   10                  15

Phe Ala Thr Val Ser Leu Ser Leu Ser Thr Cys Thr Thr Leu Asp Phe
            20                  25                  30

Gly His Ile Lys Lys Lys Arg Val Glu Ala Ile Arg Gly Gln Ile Leu
        35                  40                  45

Ser Lys Leu Arg Leu Thr Ser Pro Pro Glu Pro Thr Val Met Thr His
    50                  55                  60

Val Pro Tyr Gln Val Leu Ala Leu Tyr Asn Ser Thr Arg Glu Leu Leu
65                  70                  75                  80

Glu Glu Met His Gly Glu Arg Glu Glu Gly Cys Thr Gln Glu Asn Thr
                85                  90                  95

Glu Ser Glu Tyr Tyr Ala Lys Glu Ile His Lys Phe Asp Met Ile Gln
            100                 105                 110

Gly Leu Ala Glu His Asn Glu Leu Ala Val Cys Pro Lys Gly Ile Thr
            115                 120                 125

Ser Lys Val Phe Arg Phe Asn Val Ser Ser Val Glu Lys Asn Arg Thr
    130                 135                 140

Asn Leu Phe Arg Ala Glu Phe Arg Val Leu Arg Val Pro Asn Pro Ser
145                 150                 155                 160

Ser Lys Arg Asn Glu Gln Arg Ile Glu Leu Phe Gln Ile Leu Arg Pro
                165                 170                 175

Asp Glu His Ile Ala Lys Gln Arg Tyr Ile Gly Gly Lys Asn Leu Pro
            180                 185                 190

Thr Arg Gly Thr Ala Glu Trp Leu Ser Phe Asp Val Thr Asp Thr Val
            195                 200                 205

Arg Glu Trp Leu Leu Arg Arg Glu Ser Asn Leu Gly Leu Glu Ile Ser
    210                 215                 220

Ile His Cys Pro Cys His Thr Phe Gln Pro Asn Gly Asp Ile Leu Glu
225                 230                 235                 240

Asn Ile His Glu Val Met Glu Ile Lys Phe Lys Gly Val Asp Asn Glu
                245                 250                 255

Asp Asp His Gly Arg Gly Asp Leu Gly Arg Leu Lys Lys Gln Lys Asp
            260                 265                 270

His His Asn Pro His Leu Ile Leu Met Met Ile Pro Pro His Arg Leu
        275                 280                 285

Asp Asn Pro Gly Gln Gly Gly Gln Arg Lys Lys Arg Ala Leu Asp Thr
    290                 295                 300

Asn Tyr Cys Phe Arg Asn Leu Glu Glu Asn Cys Cys Val Arg Pro Leu
305                 310                 315                 320

Tyr Ile Asp Phe Arg Gln Asp Leu Gly Trp Lys Trp Val His Glu Pro
                325                 330                 335

Lys Gly Tyr Tyr Ala Asn Phe Cys Ser Gly Pro Cys Pro Tyr Leu Arg
            340                 345                 350

Ser Ala Asp Thr Thr His Ser Thr Val Leu Gly Leu Tyr Asn Thr Leu
```

-continued

```
          355                 360                 365

Asn Pro Glu Ala Ser Ala Ser Pro Cys Cys Val Pro Gln Asp Leu Glu
    370                 375                 380

Pro Leu Thr Ile Leu Tyr Tyr Val Gly Arg Thr Pro Lys Val Glu Gln
385                 390                 395                 400

Leu Ser Asn Met Val Val Lys Ser Cys Lys Cys Ser
                405                 410

<210> SEQ ID NO 24
<211> LENGTH: 300
<212> TYPE: PRT
<213> ORGANISM: Homo sapiens

<400> SEQUENCE: 24

Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
                20                  25                  30

Leu Ile Leu Val Val Val Leu Ala Val Val Val Pro Arg Trp Arg Gln
        35                  40                  45

Gln Trp Ser Gly Pro Gly Thr Thr Lys Arg Phe Pro Glu Thr Val Leu
    50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
                100                 105                 110

Gly Thr Gln Thr Val Pro Cys Asn Lys Ile Leu Leu Trp Ser Arg Ile
            115                 120                 125

Lys Asp Leu Ala His Gln Phe Thr Gln Val Gln Arg Asp Met Phe Thr
    130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
        195                 200                 205

Asn Gly Ser Arg Ser Lys Ile Phe Asp Lys Asn Ser Thr Phe Gly Ser
    210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Gln
                260                 265                 270

Phe Ser Cys Lys Asn Ile Tyr Arg Pro Asp Lys Phe Leu Gln Cys Val
        275                 280                 285

Lys Asn Pro Glu Asp Ser Ser Cys Thr Ser Glu Ile
    290                 295                 300

<210> SEQ ID NO 25
<211> LENGTH: 449
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Lys Glu Ala Pro Gly Gln Arg Leu Glu Trp Ile
            35                  40                  45

Gly Tyr Ile Tyr Pro Gly Gln Gly Gly Thr Asn Tyr Asn Gln Lys Phe
        50                  55                  60

Gln Gly Arg Ala Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Thr Gly Gly Leu Arg Arg Ala Tyr Phe Thr Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Ala Gly
225                 230                 235                 240

Pro Asp Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Leu Pro Glu Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
```

-continued

```
            370             375             380
Glu Ser Asn Gly Gln Pro Glu Asn Asn Tyr Lys Thr Thr Pro Pro Val
385             390             395             400

Leu Asp Ser Asp Gly Ser Phe Phe Leu Tyr Ser Lys Leu Thr Val Asp
            405             410             415

Lys Ser Arg Trp Gln Gln Gly Asn Val Phe Ser Cys Ser Val Met His
            420             425             430

Glu Ala Leu His Asn His Tyr Thr Gln Lys Ser Leu Ser Leu Ser Pro
        435             440             445

Gly

<210> SEQ ID NO 26
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Asp Ile Val Leu Thr Gln Ser Pro Ala Thr Leu Ser Leu Ser Pro Gly
1               5               10              15

Glu Arg Ala Thr Ile Ser Cys Arg Ala Ser Gln Ser Val Ser Ser Tyr
            20              25              30

Gly Gln Gly Phe Met His Trp Tyr Gln Gln Lys Pro Gly Gln Pro Pro
        35              40              45

Arg Leu Leu Ile Tyr Gly Ala Ser Ser Arg Ala Thr Gly Ile Pro Ala
    50              55              60

Arg Phe Ser Gly Ser Gly Ser Gly Thr Asp Phe Thr Leu Thr Ile Ser
65              70              75              80

Pro Leu Glu Pro Glu Asp Phe Ala Val Tyr Tyr Cys Gln Gln Asn Lys
            85              90              95

Glu Asp Pro Trp Thr Phe Gly Gly Gly Thr Lys Leu Glu Ile Lys Arg
            100             105             110

Thr Val Ala Ala Pro Ser Val Phe Ile Phe Pro Pro Ser Asp Glu Gln
        115             120             125

Leu Lys Ser Gly Thr Ala Ser Val Val Cys Leu Leu Asn Asn Phe Tyr
    130             135             140

Pro Arg Glu Ala Lys Val Gln Trp Lys Val Asp Asn Ala Leu Gln Ser
145             150             155             160

Gly Asn Ser Gln Glu Ser Val Thr Glu Gln Asp Ser Lys Asp Ser Thr
            165             170             175

Tyr Ser Leu Ser Ser Thr Leu Thr Leu Ser Lys Ala Asp Tyr Glu Lys
        180             185             190

His Lys Val Tyr Ala Cys Glu Val Thr His Gln Gly Leu Ser Ser Pro
        195             200             205

Val Thr Lys Ser Phe Asn Arg Gly Glu Cys
    210             215

<210> SEQ ID NO 27
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

-continued

<400> SEQUENCE: 27

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Lys Glu Ala Pro Gly Gln Arg Leu Glu Trp Ile
        35                  40                  45

Gly Tyr Ile Tyr Pro Gly Gln Gly Gly Thr Asn Tyr Asn Gln Lys Phe
    50                  55                  60

Gln Gly Arg Ala Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Thr Gly Gly Leu Arg Arg Ala Tyr Phe Thr Tyr Trp Gly Gln
            100                 105                 110

Gly Thr Leu Val Thr Val Ser Ser
        115                 120

<210> SEQ ID NO 28
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Asp Ile Val Leu Thr Gln Ser Pro Ala Thr Leu Ser Leu Ser Pro Gly
1               5                   10                  15

Glu Arg Ala Thr Ile Ser Cys Arg Ala Ser Gln Ser Val Ser Ser Tyr
            20                  25                  30

Gly Gln Gly Phe Met His Trp Tyr Gln Gln Lys Pro Gly Gln Pro Pro
        35                  40                  45

Arg Leu Leu Ile Tyr Gly Ala Ser Ser Arg Ala Thr Gly Ile Pro Ala
    50                  55                  60

Arg Phe Ser Gly Ser Gly Ser Gly Thr Asp Phe Thr Leu Thr Ile Ser
65                  70                  75                  80

Pro Leu Glu Pro Glu Asp Phe Ala Val Tyr Tyr Cys Gln Gln Asn Lys
                85                  90                  95

Glu Asp Pro Trp Thr Phe Gly Gly Gly Thr Lys Leu Glu Ile Lys
            100                 105                 110

<210> SEQ ID NO 29
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Gly Tyr Thr Phe Thr Ser Tyr Ala
1               5

<210> SEQ ID NO 30
<211> LENGTH: 8
<212> TYPE: PRT

<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Ile Tyr Pro Gly Gln Gly Gly Thr
1               5

<210> SEQ ID NO 31
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Ala Arg Thr Gly Gly Leu Arg Arg Ala Tyr Phe Thr Tyr
1               5                   10

<210> SEQ ID NO 32
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Gln Ser Val Ser Ser Tyr Gly Gln Gly Phe
1               5                   10

<210> SEQ ID NO 33
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Gly Ala Ser
1

<210> SEQ ID NO 34
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Gln Gln Asn Lys Glu Asp Pro Trp Thr
1               5

<210> SEQ ID NO 35
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:

-continued

Synthetic polypeptide"

<400> SEQUENCE: 35

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Gly Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Phe Arg Gly Ala Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Ala Gly Pro Asp Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Leu Pro Glu Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400
```

```
Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445
```

<210> SEQ ID NO 36
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

```
Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Gly Leu Gln Pro
65                  70                  75                  80

Glu Asp Ser Ala Thr Tyr Tyr Cys Leu Gln Asp Tyr Ile Tyr Tyr Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 37
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
```

-continued

```
                20                25                30

Gly Met His Trp Val Arg Gln Ala Pro Gly Lys Gly Leu Glu Trp Val
            35                40                45

Ala Val Ile Trp Tyr Asp Gly Ser Asn Lys Tyr Tyr Ala Asp Ser Val
        50                55                60

Lys Gly Arg Phe Thr Ile Ser Gly Asp Asn Ser Lys Asn Thr Leu Tyr
65                70                75                80

Leu Gln Met Asn Ser Leu Arg Ala Glu Asp Thr Ala Val Tyr Tyr Cys
                85                90                95

Ala Arg Met Phe Arg Gly Ala Phe Asp Tyr Trp Gly Gln Gly Thr Leu
            100                105                110

Val Thr Val Ser Ser
            115
```

<210> SEQ ID NO 38
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 38

```
Ala Ile Gln Met Thr Gln Ser Pro Ser Ser Leu Ser Ala Ser Val Gly
1                5                10                15

Asp Arg Val Thr Ile Thr Cys Arg Ala Ser Gln Gly Ile Arg Asn Asp
            20                25                30

Leu Gly Trp Tyr Gln Gln Lys Pro Gly Lys Ala Pro Lys Leu Leu Ile
            35                40                45

Tyr Ala Ala Ser Ser Leu Gln Ser Gly Val Pro Ser Arg Phe Ser Gly
        50                55                60

Ser Gly Ser Gly Thr Asp Phe Thr Leu Thr Ile Ser Gly Leu Gln Pro
65                70                75                80

Glu Asp Ser Ala Thr Tyr Tyr Cys Leu Gln Asp Tyr Ile Tyr Tyr Pro
                85                90                95

Thr Phe Gly Gln Gly Thr Lys Val Glu Ile Lys
            100                105
```

<210> SEQ ID NO 39
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 39

```
Gly Phe Thr Phe Ser Ser Tyr Gly
1                5
```

<210> SEQ ID NO 40
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 40

-continued

```
Ile Trp Tyr Asp Gly Ser Asn Lys
1               5

<210> SEQ ID NO 41
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Ala Arg Met Phe Arg Gly Ala Phe Asp Tyr
1               5                   10

<210> SEQ ID NO 42
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Gln Gly Ile Arg Asn Asp
1               5

<210> SEQ ID NO 43
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Ala Ala Ser
1

<210> SEQ ID NO 44
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Leu Gln Asp Tyr Ile Tyr Tyr Pro Thr
1               5
```

COMBINATION THERAPIES AGAINST CANCER TARGETING CD38 AND TGF-β

CROSS REFERENCE TO RELATED APPLICATIONS

This application is a national stage application under 35 U.S.C § 371 of International Patent Application No. PCT/IB2019/055885, filed on Jul. 10, 2019, which claims priority from European Application 19305470.7, filed Apr. 11, 2019, and United States Provisional Patent Application 62/696,198, filed Jul. 10, 2018. The disclosure of that application is disclosures of those applications are incorporated by reference herein in their entirety.

SEQUENCE LISTING

The instant application contains a Sequence Listing which has been submitted electronically in ASCII format and is hereby incorporated by reference in its entirety. The electronic copy of the Sequence Listing, created on Jul. 9, 2019, is named 022548_WO025_SL.txt and is 52,428 bytes in size.

BACKGROUND OF THE INVENTION

Transforming growth factor beta (TGF-β) is a cytokine that regulates diverse biologic processes, such as extracellular matrix formation, wound healing, embryonic development, bone development, hematopoiesis, immune and inflammatory responses, and malignant transformation. Deregulation of TGF-β leads to pathological conditions, e.g., birth defects, cancer, chronic inflammation, and autoimmune and fibrotic diseases.

TGF-β has three known isoforms—TGF-β1, 2, and 3. The three isoforms are pleiotropic in their function and are expressed in different patterns across cell and tissue types. They have similar in vitro activities, but individual knockouts in specific cell types suggest non-identical roles in vivo despite their shared ability to bind to the same receptor (Akhurst et al., Nat Rev Drug Discov 11(10):790-811 (2012)).

Upon TGF-β binding to TGFβRII, the constitutive kinase activity of the receptor phosphorylates and activates TGFβRI, which phosphorylates SMAD2/3, allowing it to associate with SMAD4, which then localizes to the nucleus and initiates transcription of TGF-β-responsive genes. Id. In addition to this canonical signaling cascade, a non-canonical pathway transmits signals through other factors including p38 MAPK, PI3K, AKT, JUN, JNK, and NF-κB. TGF-β signaling is also modulated by other pathways, including WNT, Hedgehog, Notch, INF, TNF, and RAS. Thus, the end result of TGF-β signaling is a crosstalk of all of these signaling pathways that integrates the state and environment of the cell. Id.

CD38 is a 45 kD type II transmembrane glycoprotein with a long C-terminal extracellular domain and a short N-terminal cytoplasmic domain. The CD38 protein is a bifunctional ectoenzyme that catalyzes the conversion of $NAD^+$ into cyclic ADP-ribose (cADPR) and also hydrolyzes cADPR into ADP-ribose. During ontogeny, CD38 appears on CD34-positive committed stem cells and lineage-committed progenitors of lymphoid, erythroid and myeloid cells. CD38 expression persists mostly in the lymphoid lineage with varying expression levels at different stages of T and B cell development.

CD38 is upregulated in many hematopoietic malignancies and in cell lines derived from various hematopoietic malignancies, including non-Hodgkin's lymphoma (NHL), Burkitt's lymphoma (BL), multiple myeloma (MM), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's lymphoma (HL), and chronic myeloid leukemia (CML). On the other hand, most primitive pluripotent stem cells of the hematopoietic system are CD38-negative. CD38 expression in hematopoietic malignancies and its correlation with disease progression make CD38 an attractive target for antibody therapy.

SUMMARY OF THE INVENTION

Provided herein are combination therapies targeting CD38 and TGF-β. The present inventors have found that an anti-TGF-β antibody can block the ability of TGF-β to dampen the anti-tumor effect of an anti-CD38 antibody (e.g., TGF-β can inhibit NK cell-mediated ADCC of an anti-CD38 antibody). Compared to currently available treatments for cancer, including antibody treatments, the combination therapies provided herein may provide a superior clinical efficacy.

Accordingly, provided herein is a method for enhancing the efficacy of an agent that specifically binds to CD38 with an agent that specifically binds to TGF-β. In some embodiments, provided herein is a method of treating cancer in a patient (e.g., a human patient) by administering to the patient an agent that specifically binds to human CD38 and an agent that specifically binds to human TGF-β. In some embodiments, the agent that specifically binds to human CD38 is an anti-CD38 antibody or an antigen-binding fragment thereof. In certain embodiments, the anti-CD38 antibody is capable of killing a CD38-positive cell by apoptosis, antibody-dependent cell-mediated cytotoxicity (ADCC), and/or complement-dependent cytotoxicity (CDC), wherein killing the CD38-positive cell by apoptosis can occur in the absence of stroma cells or stroma-derived cytokines. In some embodiments, the agent that specifically binds to human TGF-β is a pan-specific anti-TGF-β antibody or an antigen-binding fragment thereof.

In some embodiments, provided herein is a method of treating cancer in a human patient in need thereof, administering to the patient an anti-CD38 antibody and an anti-TGF-β antibody or an antigen-fragment thereof.

In some embodiments, the anti-CD38 antibody:
a) has HCDR1-3 and LCDR1-3 comprising the amino acid sequences of SEQ ID NOs: 15-20, respectively;
b) has a heavy chain variable domain and a light chain variable domain comprising the amino acid sequences of SEQ ID NOs: 13 and 14, respectively; or
c) has a heavy chain comprising the amino acid sequence of SEQ ID NO: 11 and a light chain comprising the amino acid sequence of SEQ ID NO: 12.

In some embodiments, the anti-TGF-β antibody:
a) has HCDR1-3 and LCDR1-3 comprising the amino acid sequences of SEQ ID NOs: 5-10, respectively;
b) has a heavy chain variable domain and a light chain variable domain comprising the amino acid sequences of SEQ ID NOs: 3 and 4, respectively; or.
c) has a heavy chain comprising the amino acid sequence of SEQ ID NO: 1 and a light chain comprising the amino acid sequence of SEQ ID NO: 2.

In some embodiments, the anti-CD38 antibody has heavy chain CDR1 (HCDR1), HCDR2, HCDR3, light chain CDR1

(LCDR1), LCDR2, and LCDR3 comprising the amino acid sequences of SEQ ID NOs: 15-20, respectively, and the anti-TGF-β antibody or antigen-binding fragment thereof has HCDR1, HCDR2, HCDR3, LCDR1, LCDR2, and LCDR3 comprising the amino acid sequences of SEQ ID NOs: 5-10, respectively. In certain embodiments, the anti-CD38 antibody comprises a heavy chain variable domain (V$_H$) and a light chain variable domain (V$_L$) comprising the amino acid sequences of SEQ ID NOs: 13 and 14, respectively; and the anti-TGF-β antibody comprises a V$_H$ and a V$_L$ comprising the amino acid sequences of SEQ ID NOs: 3 and 4, respectively. In particular embodiments, the anti-CD38 antibody has a heavy chain (HC) and a light chain (LC) comprising the amino acid sequences of SEQ ID NOs: 11 and 12, respectively; and the anti-TGF-β antibody has a heavy chain and a light chain comprising the amino acid sequences of SEQ ID NOs: 1 and 2, respectively.

In any of the embodiments provided herein, the anti-CD38 antibody may comprise a human IgG$_1$ Fc region and the anti-TGF-β antibody may comprise a human IgG$_4$ Fc region.

Also provided herein is a method of treating multiple myeloma in a human patient in need thereof, comprising administering to the patient an anti-CD38 antibody that comprises a heavy chain variable domain amino acid sequence of SEQ ID NO: 13 and a light chain variable domain amino acid sequence of SEQ ID NO: 14, and an anti-TGF-β antibody that comprises a heavy chain variable domain amino acid sequence of SEQ ID NO: 3 and a light chain variable domain amino acid sequence of SEQ ID NO: 4.

Also provided herein is a method of treating multiple myeloma in a human patient in need thereof, comprising administering to the patient an anti-CD38 antibody that comprises a heavy chain amino acid sequence of SEQ ID NO: 11 and a light chain amino acid sequence of SEQ ID NO: 12, and an anti-TGF-β antibody that comprises a heavy chain amino acid sequence of SEQ ID NO: 1 and a light chain amino acid sequence of SEQ ID NO: 2.

In any of the embodiments provided herein, the anti-CD38 antibody and the anti-TGF-β antibody or fragment may be administered to the patient sequentially.

Also provided herein is an anti-CD38 antibody for use in treating cancer in a human patient in need thereof in combination with an anti-TGF-β antibody, and the use of an anti-CD38 antibody for the manufacture of a medicament for treating cancer in a human patient in need thereof in combination with an anti-TGF-β antibody. In some embodiments, the anti-CD38 antibody a) has HCDR1-3 and LCDR1-3 comprising the amino acid sequences of SEQ ID NOs: 15-20, respectively;

b) has a heavy chain variable domain and a light chain variable domain comprising the amino acid sequences of SEQ ID NOs: 13 and 14, respectively; or c) has a heavy chain comprising the amino acid sequence of SEQ ID NO: 11 and a light chain comprising the amino acid sequence of SEQ ID NO: 12.

Also provided herein is an anti-TGF-β antibody for use in treating cancer in a human patient in need thereof in combination with an anti-CD38 antibody, and the use of an anti-TGF-β antibody for the manufacture of a medicament for treating cancer in a human patient in need thereof in combination with an anti-CD38 antibody. In some embodiments, the anti-TGF-β antibody a) has HCDR1-3 and LCDR1-3 comprising the amino acid sequences of SEQ ID NOs: 5-10, respectively;

b) has a heavy chain variable domain and a light chain variable domain comprising the amino acid sequences of SEQ ID NOs: 3 and 4, respectively; or c) has a heavy chain comprising the amino acid sequence of SEQ ID NO: 1 and a light chain comprising the amino acid sequence of SEQ ID NO: 2.

In some embodiments of the methods, antibodies for use, and uses of antibodies described herein, the cancer is CD38-positive.

In some embodiments of the methods, antibodies for use, and uses of antibodies described herein, the cancer is selected from the group consisting of multiple myeloma, non-Hodgkin's lymphoma, Hodgkin's lymphoma, diffuse large B-cell lymphoma, peripheral T-cell lymphoma, hairy cell leukemia, chronic lymphocytic leukemia, chronic myeloid leukemia, acute myeloid leukemia, acute lymphocytic leukemia, melanoma, glioblastoma, lung cancer, cutaneous squamous cell carcinoma, colorectal cancer, breast cancer, ovarian cancer, head and neck cancer, hepatocellular carcinoma, urothelial cancer, and renal cell carcinoma.

In some embodiments of the methods, antibodies for use, and uses of antibodies described herein, the cancer is a hematological malignancy.

In some embodiments of the methods, antibodies for use, and uses of antibodies described herein, the cancer is multiple myeloma. In particular embodiments, the treatments described herein result in less bone destruction than treatment with the anti-CD38 antibody alone, and/or enhance bone formation resulting in bone remodeling and/or bone healing, in multiple myeloma patients.

Accordingly, in some embodiments, provided herein is a method for reducing bone destruction in a human multiple myeloma patient comprising administering to the patient an agent that specifically binds to human CD38 as described herein (e.g., an anti-CD38 antibody) and an agent that specifically binds to human TGF-β as described herein (e.g., an anti-TGF-β antibody). Also provided herein is an anti-TGF-β antibody as described herein for use in reducing bone destruction in a human multiple myeloma patient in combination with an anti-CD38 antibody, and the use of an anti-TGF-β antibody for the manufacture of a medicament for reducing bone destruction in a human multiple myeloma patient in combination with an anti-CD38 antibody.

Also provided herein is a method for enhancing bone formation resulting in bone remodeling and/or bone healing in a multiple myeloma patient comprising administering to the patient an agent that specifically binds to human CD38 as described herein (e.g., an anti-CD38 antibody) and an agent that specifically binds to human TGF-β as described herein (e.g., an anti-TGF-β antibody). Also provided herein is an anti-TGF-β antibody as described herein for use in enhancing bone formation in a human multiple myeloma patient in combination with an anti-CD38 antibody, and the use of an anti-TGF-β antibody for the manufacture of a medicament for enhancing bone formation in a human multiple myeloma patient in combination with an anti-CD38 antibody.

In some embodiments of the methods, antibodies for use, and uses of antibodies described herein, the cancer is refractory to treatment with Ab2 or treatment with daratumumab, or refractory to both treatments. In some embodiments, the patient has relapsed or refractory multiple myeloma and has received at least one prior therapy or at least two prior therapies.

Also provided herein is an article of manufacture comprising an anti-CD38 antibody and an anti-TGF-β antibody, wherein said article of manufacture is suitable for treating cancer in a patient, e.g., in a treatment method described herein. In some embodiments, the anti-CD38 antibody a) has HCDR1-3 and LCDR1-3 comprising the amino acid sequences of SEQ ID NOs: 15-20, respectively;

b) has a heavy chain variable domain and a light chain variable domain comprising the amino acid sequences of SEQ ID NOs: 13 and 14, respectively; or c) has a heavy chain comprising the amino acid sequence of SEQ ID NO: 11 and a light chain comprising the amino acid sequence of SEQ ID NO: 12; and the anti-TGF-β antibody a) has HCDR1-3 and LCDR1-3 comprising the amino acid sequences of SEQ ID NOs: 5-10, respectively;

b) has a heavy chain variable domain and a light chain variable domain comprising the amino acid sequences of SEQ ID NOs: 3 and 4, respectively; or c) has a heavy chain comprising the amino acid sequence of SEQ ID NO: 1 and a light chain comprising the amino acid sequence of SEQ ID NO: 2.

BRIEF DESCRIPTION OF THE DRAWINGS

FIG. 4 is a graph showing the effect of 0.1, 1, and 10 ng/mL TGF-β on Ab2-mediated ADCC of NCI-H929 cells.

DETAILED DESCRIPTION OF THE INVENTION

Figure 1:
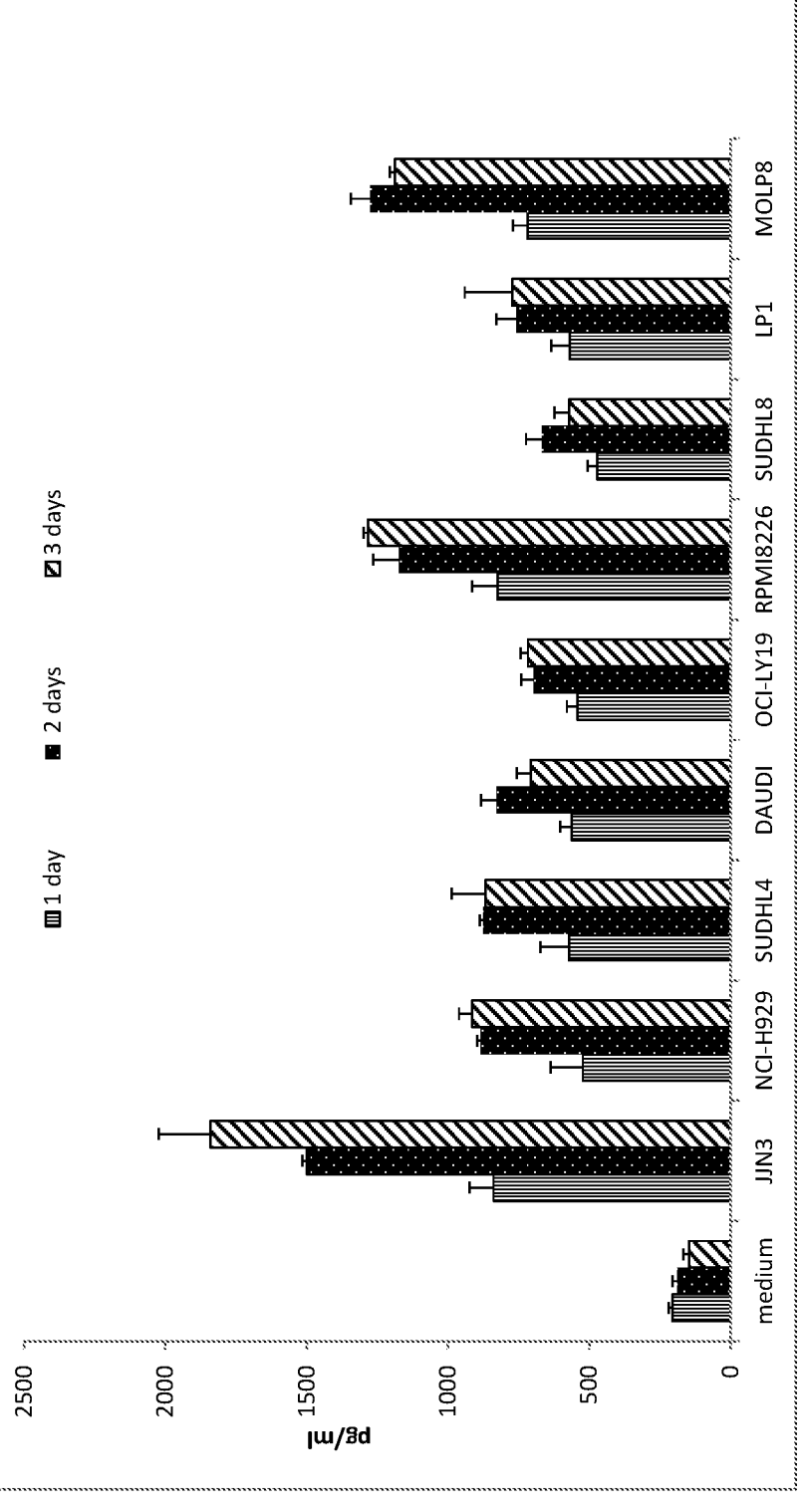
FIG. 1 is a graph showing the release of TGF-β by multiple myeloma cell lines at one, two, or three days as quantified by ELISA.

The present disclosure provides new combination therapies that target human TGF-β and human CD38, e.g., by using antibodies that bind these targets. The combination therapies can be used to treat conditions such as cancer. Unless otherwise stated, "TGF-β" refers to human TGF-β herein. The polypeptide sequences of the three isoforms of human TGF-β (TGF-β1, TGF-β2, and TGF-β3) are available under SwissProt Accession Nos. P01137, P08112, and P10600, respectively, shown here as SEQ ID NOs: 21-23. Unless otherwise stated, "CD38" refers to human CD38 herein. The human CD38 polypeptide sequence is available under Genbank Accession No. NP_001766, shown here as SEQ ID NO: 24.

As used herein, the term "antibody" (Ab) or "immunoglobulin" (Ig) refers to a tetrameric protein comprising two heavy (H) chains (about 50-70 kDa) and two light (L) chains (about 25 kDa) inter-connected by disulfide bonds. Each heavy chain is comprised of a heavy chain variable domain (V$_H$) and a heavy chain constant region (C$_H$). Each light chain is composed of a light chain variable domain (V$_L$) and a light chain constant region (C$_L$). The V$_H$ and V$_L$ domains can be subdivided further into regions of hypervariability, called "complementarity-determining regions" (CDRs), interspersed with regions that are more conserved, called "framework regions" (FRs). Each V$_H$ or V$_L$ is composed of three CDRs and four FRs, arranged from amino-terminus to carboxyl-terminus in the following order: FR1, CDR1, FR2, CDR2, FR3, CDR3, and FR4. The assignment of amino acids to each region may be in accordance with IMGT® definitions (Lefranc et al., Dev Comp Immunol 27(1):55-77 (2003)); or the definitions of Kabat, Sequences of Proteins of Immunological Interest (National Institutes of Health, Bethesda, MD (1987 and 1991)); Chothia & Lesk, J. Mol. Biol. 196:901-917 (1987); or Chothia et al., Nature 342: 878-883 (1989).

The term "affinity" refers to a measure of the attraction between an antigen and an antibody. The intrinsic attractiveness of the antibody for the antigen is typically expressed as the binding affinity equilibrium constant (K$_D$) of a particular antibody-antigen interaction. An antibody is said to specifically bind to an antigen when the K$_D$ is less than $10^{-7}$ M, such as less than $10^{-8}$ M (e.g., 1-9 nM), as determined by, e.g., surface plasmon resonance or Bio-Layer Interferometry.

The term "k$_{off}$" refers to the dissociation rate constant of a particular antibody-antigen interaction. A k$_{off}$ dissociation rate constant can be measured, e.g., by Bio-Layer Interferometry.

The term "epitope" as used herein refers to a portion (determinant) of an antigen that specifically binds to an antibody. Epitopic determinants generally consist of chemically active surface groupings of molecules such as amino acids or carbohydrate or sugar side chains and generally have specific three-dimensional structural characteristics, as well as specific charge characteristics. An epitope may be "linear" or "conformational." In a linear epitope, all of the points of interaction between a protein (e.g., an antigen) and an interacting molecule (such as an antibody) occur linearly along the primary amino acid sequence of the protein. In a conformational epitope, the points of interaction occur across amino acid residues on the protein that are separated from one another in the primary amino acid sequence. Once a desired epitope on an antigen is determined, it is possible to generate antibodies to that epitope using techniques well known in the art. For example, an antibody to a linear epitope may be generated, e.g., by immunizing an animal with a peptide having the amino acid residues of the linear epitope. An antibody to a conformational epitope may be generated, e.g., by immunizing an animal with a mini-domain containing the relevant amino acid residues of the conformational epitope. An antibody to a particular epitope can also be generated, e.g., by immunizing an animal with the target molecule of interest or a relevant portion thereof, then screening for binding to the epitope.

One can determine whether an antibody binds to the same epitope as, or competes for binding with, an antibody as described herein by using methods known in the art, including, without limitation, competition assays, epitope binning, and alanine scanning. In some embodiments, the test antibody and an antibody as described herein bind to at least one common residue (e.g., at least two, three, four, five, six, seven, eight, nine, or ten residues) on the target protein (i.e., TGF-β or CD38). In further embodiments, the contact residues on the target protein are completely identical between the test antibody and the antibody as described herein. In one embodiment, one allows the antibody as described herein to bind to the target protein under saturating conditions and then measures the ability of the test antibody to bind to the target protein. If the test antibody is able to bind to the target protein at the same time as the reference antibody, then the test antibody binds to a different epitope than the reference antibody. However, if the test antibody is not able to bind to the target protein at the same time, then the test antibody binds to the same epitope, an overlapping epitope, or an epitope that is in close proximity to the epitope bound by the antibody as described herein. This experiment can be performed using, e.g., ELISA, RIA, BIACORE™, SPR, Bio-Layer Interferometry or flow cytometry. To test whether an antibody cross-competes with another antibody, one may use the competition method described above in two directions, i.e., determining if the known antibody blocks the test antibody and vice versa.

The term "humanize" refers to the fact that where an antibody is wholly or partially of non-human origin (for example, a murine antibody obtained from immunization of mice with an antigen of interest, or a chimeric antibody based on such a murine antibody), it is possible to replace certain amino acids, in particular in the framework regions and constant regions of the heavy and light chains, in order to avoid or minimize an immune response in humans. Although it is not possible to precisely predict the immunogenicity and thereby the human anti-antibody response of a particular antibody, non-human antibodies tend to be more immunogenic in humans than human antibodies. Chimeric antibodies, where the foreign (e.g., rodent) constant regions have been replaced with sequences of human origin, have been shown to be generally less immunogenic than antibodies of fully foreign origin, and the trend in therapeutic antibodies is towards humanized or fully human antibodies. Chimeric antibodies or other antibodies of non-human origin thus can be humanized to reduce the risk of a human anti-antibody response.

For chimeric antibodies, humanization typically involves modification of the framework regions of the variable domain sequences. Amino acid residues that are part of complementarity determining regions (CDRs) most often will not be altered in connection with humanization, although in certain cases it may be desirable to alter individual CDR amino acid residues, for example to remove a glycosylation site, a deamidation site, an aspartate isomerization site or an undesired cysteine or methionine residue. N-linked glycosylation occurs by attachment of an oligosaccharide chain to an asparagine residue in the tripeptide sequence Asn-X-Ser or Asn-X-Thr, where X may be any amino acid except Pro. Removal of an N-glycosylation site may be achieved by mutating either the Asn or the Ser/Thr residue to a different residue, preferably by way of conservative substitution. Deamidation of asparagine and glutamine residues can occur depending on factors such as pH and surface exposure. Asparagine residues are particularly susceptible to deamidation, primarily when present in the sequence Asn-Gly, and to a lesser extent in other dipeptide sequences such as Asn-Ala. When such a deamidation site, in particular Asn-Gly, is present in a CDR sequence, it may therefore be desirable to remove the site, typically by conservative substitution to remove one of the implicated residues.

Numerous methods for humanization of an antibody sequence are known in the art; see, e.g., the review by Almagro & Fransson, Front Biosci. 13:1619-1633 (2008). One commonly used method is CDR grafting, which for, e.g., a murine-derived chimeric antibody involves identification of human germline gene counterparts to the murine variable domain genes and grafting of the murine CDR sequences into this framework. The specificity of an antibody's interaction with a target antigen resides primarily in the amino acid residues located in the six CDRs of the heavy and light chain. The amino acid sequences within CDRs are therefore much more variable between individual antibodies than sequences outside of CDRs. Because CDR sequences are responsible for most antibody-antigen interactions, it is possible to express recombinant antibodies that mimic the properties of a specific naturally occurring antibody, or more generally any specific antibody with a given amino acid sequence, e.g., by constructing expression vectors that express CDR sequences from the specific antibody grafted into framework sequences from a different antibody. As a result, it is possible to "humanize" a non-human antibody and still substantially maintain the binding specificity and affinity of the original antibody. CDR grafting may be based on the Kabat CDR definitions, although a more recent publication (Magdelaine-Beuzelin et al., Crit Rev. Oncol Hematol. 64:210-225 (2007)) has suggested that the IMGT® definition (the international ImMunoGeneTics Information System®, www.imgt.org) may improve the result of the humanization (see Lefranc et al., Dev. Comp Immunol. 27:55-77 (2003)).

In some cases, CDR grafting may reduce the binding specificity and affinity, and thus the biological activity, of a CDR-grafted non-human antibody as compared to the parent antibody from which the CDRs are obtained. Back mutations (sometimes referred to as "framework repair") may be introduced at selected positions of the CDR-grafted antibody, typically in the framework regions, in order to reestablish the binding specificity and affinity of the parent antibody. Positions for possible back mutations can be identified using information available in the literature and in antibody databases. Amino acid residues that are candidates for back mutations are typically those that are located at the surface of an antibody molecule, while residues that are buried or that have a low degree of surface exposure will not normally be altered.

An alternative humanization technique to CDR grafting and back mutation is resurfacing, in which non-surface exposed residues of non-human origin are retained, while surface residues are altered to human residues.

In certain cases, it may be desirable to alter one or more CDR amino acid residues in order to improve binding affinity to the target epitope. This is known as "affinity maturation." Various affinity maturation methods are known in the art, for example, the in vitro scanning saturation mutagenesis method described by Burks et al., Proc Natl Acad Sci USA, 94:412-417 (1997), and the stepwise in vitro affinity maturation method of Wu et al., Proc Natl Acad Sci USA 95:6037-6042 (1998).

The term "human antibody" refers to an antibody in which the variable domain and constant region sequences are derived from human sequences. The term encompasses antibodies with sequences derived from human genes, but those sequences have been modified, e.g., to decrease immunogenicity, increase affinity, and increase stability. The term encompasses antibodies produced recombinantly in nonhuman cells, which may impart glycosylation not typical of human cells. The term also encompasses antibodies produced in transgenic nonhuman organisms with human antibody genes.

The term "antigen-binding portion" or "antigen-binding fragment" of an antibody refers to a portion or fragment of an antibody that retains the ability to specifically bind to an antigen. In some embodiments, an antigen-binding fragment of the present disclosure is a Fab, Fab', F(ab')$_2$, Fv, or scFv fragment. In certain embodiments, an antigen-binding fragment of the present disclosure is an F(ab')$_2$ fragment, which is a bivalent fragment comprising two Fab fragments linked by a disulfide bridge at the hinge region (Fab is a monovalent antibody fragment consisting of the $V_L$, $V_H$, $C_L$ and $C_{H1}$ domains). In some embodiments, an antigen-binding fragment of the present disclosure may also comprise a $C_{H2}$ or $C_{H3}$ domain. Antibody fragments can be prepared, for example, from whole antibodies using conventional techniques, such as papain or pepsin digestion of whole antibodies. Moreover, antibodies, antibody fragments and immunoadhesion molecules can be obtained using standard recombinant DNA techniques, e.g., as described herein.

The antibodies and antigen-binding fragments described herein may be isolated. The term "isolated protein", "isolated polypeptide" or "isolated antibody" refers to a protein, polypeptide or antibody that by virtue of its origin or source of derivation (1) is not associated with naturally associated components that accompany it in its native state, (2) is substantially free of other proteins from the same species, (3) is expressed by a cell from a different species, or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The class (isotype) and subclass of antibodies described herein may be determined by any method known in the art. In general, the class and subclass of an antibody may be determined using antibodies that are specific for a particular class and subclass of antibody. Such antibodies are available commercially. The class and subclass can be determined by ELISA and Western Blot as well as other techniques. Alternatively, the class and subclass may be determined by sequencing all or a portion of the constant regions of the heavy and/or light chains of the antibodies, comparing their amino acid sequences to the known amino acid sequences of various classes and subclasses of immunoglobulins, and determining the class and subclass of the antibodies. A preferred isotype of the present disclosure is an IgG isotype.

Agents that Inhibit TGF-β

In some embodiments, the agent that specifically binds to TGF-β used in a combination therapy described herein is an anti-TGF-β antibody or an antigen-binding fragment thereof (e.g., Ab1, fresolimumab, XOMA 089/NIS793 (Gramont et al., Oncoimmunology 6(1):e1257453 (2017)), SRK-181 (Scholar Rock), ABBV-151 (AbbVie), lerdelimumab, or metelimumab) or a TGF-β trap molecule (e.g., M7824 (Knudson et al., Oncoimmunology 7(5):e1426519 (2018)) or AVID200 (Thwaites et al., Blood 130:2532 (2017))). In certain embodiments, the anti-TGF-β antibody is a human monoclonal antibody. In some embodiments, the anti-TGF-β antibody is a pan-TGF-β-specific monoclonal antibody that is less prone to form half antibodies in comparison to prior known antibodies such as fresolimumab. In some embodiments, the anti-TGF-β antibody has superior pharmacokinetic profiles such as higher exposure in the body in comparison to fresolimumab.

In some embodiments, the anti-TGF-β antibody is an antibody described in PCT Patent Publication WO 2018/134681, PCT Patent Publication WO 2006/086469, PCT Patent Publication WO 2014/153435, U.S. Pat. No. 8,569,462, or U.S. Pat. No. 7,527,791, which are incorporated by reference in their entirety herein. In certain embodiments, the anti-TGF-β antibody is antibody Ab1, or a variant thereof, wherein the variant may, e.g., contain certain minimum amino acid changes relative to Ab1 (e.g., 1, 2, 3, 4, 5, 6, 7, 8, 9, or 10 amino acid changes, which may be, e.g., in the framework regions) without losing the antigen-binding specificity of the antibody.

Antibody Ab1 has an estimated molecular weight of 144 kD when un-glycosylated. Its heavy and light chain amino acid sequences are SEQ ID NOs: 1 and 2, respectively. These two sequences are shown below. Variable domains are italicized. CDRs are shown in boxes. The glycosylation site in the constant domain of the heavy chain is in boldface and lower case (N297). Ab1 has a human IgG$_4$ constant region where residue 228 (EU numbering) in the hinge region has been mutated from serine to proline. P228 is in box and boldface in the sequence of SEQ ID NO: 1 shown below.

(SEQ ID NO: 1)

*QVQLVQSGAE VKKPGSSVKV SCKASGYTFS* SNVIS *WVRQA PGQGLEWMG* G VIPIVDIANY

AQRFKG *RVTI TADESTSTTY MELSSLRSED TAVYYCA* TL GLVLDAMDY *W GQGTLVTVSS*

ASTKGPSVFP LAPCSRSTSE STAALGCLVK DYFPEPVTVS WNSGALTSGV HTFPAVLQSS

GLYSLSSVVT VPSSSLGTKT YTCNVDHKPS NTKVDKRVES KYGPPCP P CP APEFLGGPSV

FLFPPKPKDT LMISRTPEVT CVVVDVSQED PEVQFNWYVD GVEVHNAKTK PREEQF n STY

RVVSVLTVLH QDWLNGKEYK CKVSNKGLPS SIEKTISKAK GQPREPQVYT LPPSQEEMTK

NQVSLTCLVK GFYPSDIAVE WESNGQPENN YKTTPPVLDS DGSFFLYSRL TVDKSRWQEG

NVFSCSVMHE ALHNHYTQKS LSLSLGK

-continued (SEQ ID NO: 2)

```
ETVLTQSPGT LSLSPGERAT LSC RASQSLG SSYLA WYQQK PGQAPRLLIY GASSRAP GIP

DRFSGSGSGT DFTLTISRLE PEDFAVYYC Q QYADSPIT FG QGTRLEIKRT VAAPSVFIFP

PSDEQLKSGT ASVVCLLNNF YPREAKVQWK VDNALQSGNS QESVTEQDSK DSTYSLSSTL

TLSKADYEKH KVYACEVTHQ GLSSPVTKSF NRGEC
```

In some embodiments, an anti-TGF-β antibody or antigen-binding fragment described herein competes for binding to TGF-β with, or binds to the same epitope on TGF-β as, Ab1.

In some embodiments, an anti-TGF-β antibody described herein has a heavy chain that comprises:
    a) heavy chain CDR1-3 (HCDR1-3) that comprise the amino acid sequences of SEQ ID NOs: 5-7, respectively;
    b) a heavy chain variable domain ($V_H$) that is at least 75%, 80%, 85%, 90%, 91%, 92%, 93%, 94%, 95%, 96%, 97%, 98%, or 99% identical in sequence to the amino acid sequence of SEQ ID NO: 3;
    c) a $V_H$ that comprises the amino acid sequence of SEQ ID NO: 3; or
    d) the amino acid sequence of SEQ ID NO: 1.

In some embodiments, an anti-TGF-β antibody described herein has a light chain that comprises:
    a) light chain CDR1-3 (LCDR1-3) that comprise the amino acid sequences of SEQ ID NOs: 8-10, respectively;
    b) a light chain variable domain ($V_L$) that is at least 75%, 80%, 85%, 90%, 91%, 92%, 93%, 94%, 95%, 96%, 97%, 98%, or 99% identical in sequence to the amino acid sequence of SEQ ID NO: 4;
    c) a $V_L$ that comprises the amino acid sequence of SEQ ID NO: 4; or
    d) the amino acid sequence of SEQ ID NO: 2.

In some embodiments, an anti-TGF-β antibody described herein comprises any of the above heavy chains in combination with any of the above light chains.

In some embodiments, an anti-TGF-β antibody described herein comprises:
    a) HCDR1-3 and LCDR1-3 that comprise the amino acid sequences of SEQ ID NOs: 5-10, respectively;
    b) a $V_H$ that is at least 75%, 80%, 85%, 90%, 91%, 92%, 93%, 94%, 95%, 96%, 97%, 98%, or 99% identical in sequence to the amino acid sequence of SEQ ID NO: 3 and a $V_L$ that is at least 75%, 80%, 85%, 90%, 91%, 92%, 93%, 94%, 95%, 96%, 97%, 98%, or 99% identical in sequence to the amino acid sequence of SEQ ID NO: 4;
    c) a $V_H$ that comprises the amino acid sequence of SEQ ID NO: 3 and a $V_L$ that comprises the amino acid sequence of SEQ ID NO: 4; and
    d) an HC that comprises the amino acid sequence of SEQ ID NO: 1 and an LC that comprises the amino acid sequence of SEQ ID NO: 2.

In some embodiments, an anti-TGF-β antibody described herein (e.g., an anti-TGF-β antibody with the six CDRs or the $V_H$ and $V_L$ of Ab1) has a human IgG$_4$ constant region. In certain embodiments, residue 228 (EU numbering) in the hinge region of the IgG$_4$ constant region has been mutated from serine to proline. The constant domain of an anti-TGF-β antibody described herein can also be modified, for example, at Kabat residue L248 (e.g., by introducing the mutation L248E), to reduce any undesired effector function of the molecule.

In some embodiments, an anti-TGF-β antibody described herein has a human immunoglobulin kappa light chain region.

In some embodiments, an anti-TGF-β antibody or antigen-binding fragment described herein binds specifically to human TGF-β1, -β2, and -β3.

In some embodiments, an anti-TGF-β antibody or antigen-binding fragment described herein binds TGF-β1, -β2, and/or -β3 (e.g., TGF-β1, -β2, and -β3) with a $K_D$ of $1\times10^{-8}$ M or lower, e.g., $9\times10^{-9}$ M, $8\times10^{-9}$ M, $7\times10^{-9}$ M, $6\times10^{-9}$ M, $5\times10^{-9}$ M, $4\times10^{-9}$ M, $3\times10^{-9}$ M, $2\times10^{-9}$ M, or $1\times10^{-9}$ M. In certain embodiments, the anti-TGF-β antibody or antigen-binding fragment binds TGF-β1, -β2, and -β3 with a $K_D$ of $3\times10^{-9}$ M or lower.

In some embodiments, an anti-TGF-β antibody or antigen-binding fragment described herein has one or more of the following properties:
    a) inhibits TGF-β signal transduction;
    b) neutralizes TGF-β when assayed in a mink lung epithelial cell assay;
    c) has an EC50 of about 0.05 to 1 µg/ml as determined in an A549 cell IL-11 induction assay;
    d) inhibits the differentiation of CD4-positive T cells into inducible regulatory T cells (iTreg);
    e) alleviates the immunosuppressive tumor microenvironment;
    f) increases MIP2 levels in a patient (e.g., in the tumor tissue of a patient);
    g) increases KC/GRO levels in a patient (e.g., in the tumor tissue of a patient);
    h) promotes activation or infiltration to tumor tissue of CD8-positive T cells such as INF-γ-positive CD8-positive T cells;
    i) increases clustering of natural killer (NK) cells in a patient (e.g., in the tumor tissue of a patient); and
    j) restores the cytolytic activity of NK-92 cells after incubation with human recombinant TGF-β.

In some embodiments, an anti-TGF-β antibody or antigen-binding fragment described herein has 1, 2, 3, 4, 5, 6, 7, 8, 9, or all of said properties.

In some embodiments, an anti-TGF-β antibody or antigen-binding fragment described herein has an increased half-life, an increased exposure, or both, as compared to fresolimumab. For example, the increase is a 10%, 20%, 30%, 40%, 50%, 60%, 70%, 80%, 90%, or 100% or more increase. The exposure of a drug such as an antibody or fragment described herein is a function of the concentration of the drug in the body with respect to time. The concentration of the drug in the body often is indicated by the level of the drug in the blood, plasma, or serum. Half-life and exposure (bio-exposure) of a drug can be measured by well-known methods (e.g., as described in PCT Patent Publication WO 2018/134681).

Agents that Inhibit CD38

In some embodiments, the agent that specifically binds to CD38 used in a combination therapy described herein is an anti-CD38 antibody or an antigen-binding fragment thereof. In certain embodiments, the anti-CD38 antibody is a humanized monoclonal antibody. In some embodiments, the anti-CD38 antibody is an antibody described in U.S. Pat. No. 8,153,765, which is incorporated by reference in its entirety herein. In some embodiments, the anti-CD38 antibody is produced by a hybridoma cell line deposited at the American Type Culture Collection under deposit number PTA-7670. In some embodiments, the anti-CD38 antibody is Ab2, Ab3, Ab4, daratumumab, MOR202 (Raab et al., Blood 128:1152 (2016)), TAK-079 (Roepcke et al., Pharmacol Res Perspect 6(3):e00402 (2018)), TAK-573 (Takeda), TAK-169 (Takeda), HexaBody®-CD38 (Genmab/Janssen), an anti-CD38 SIFbody (Momenta), or TSK011010 (CASI).

In particular embodiments, the anti-CD38 antibody is antibody Ab2, or a variant thereof, wherein the variant may for example contain certain minimum amino acid changes relative to Ab2 (e.g., 1, 2, 3, 4, 5, 6, 7, 8, 9, or 10 amino acid changes, which may be, e.g., in the framework regions) without losing the antigen-binding specificity of the antibody.

The heavy and light chain amino acid sequences of Ab2 are SEQ ID NOs: 11 and 12, respectively. These two sequences are shown below. Variable domains are italicized. CDRs are shown in boxes. Ab2 has a human IgG$_1$ constant region.

b) a heavy chain variable domain (V$_H$) that is at least 75%, 80%, 85%, 90%, 91%, 92%, 93%, 94%, 95%, 96%, 97%, 98%, or 99% identical in sequence to the amino acid sequence of SEQ ID NO: 13;

c) a V$_H$ that comprises the amino acid sequence of SEQ ID NO: 13; or d) the amino acid sequence of SEQ ID NO: 11.

In some embodiments, the anti-CD38 antibody has a light chain that comprises:

a) light chain CDR1-3 (LCDR1-3) that comprise the amino acid sequences of SEQ ID NOs: 18-20, respectively;

b) a light chain variable domain (V$_L$) that is at least 75%, 80%, 85%, 90%, 91%, 92%, 93%, 94%, 95%, 96%, 97%, 98%, or 99% identical in sequence to the amino acid sequence of SEQ ID NO: 14;

c) a V$_L$ that comprises the amino acid sequence of SEQ ID NO: 14; or d) the amino acid sequence of SEQ ID NO: 12.

In some embodiments, an anti-CD38 antibody described herein comprises any of the above heavy chains in combination with any of the above light chains.

In some embodiments, an anti-CD38 antibody described herein comprises:

a) HCDR1-3 and LCDR1-3 that comprise the amino acid sequences of SEQ ID NOs: 15-20, respectively;

b) a V$_H$ that is at least 75%, 80%, 85%, 90%, 91%, 92%, 93%, 94%, 95%, 96%, 97%, 98%, or 99% identical in sequence to the amino acid sequence of SEQ ID NO: 13 and a V$_L$ that is at least 75%, 80%, 85%, 90%, 91%, 92%, 93%, 94%, 95%, 96%, 97%, 98%, or 99% identical in sequence to the amino acid sequence of SEQ ID NO: 14;

```
                                              (SEQ ID NO: 11)
QVQLVQSGAE VAKPGTSVKL SCKASGYTFT DYWMQ WVKQR PGQGLEWIG T IYPGDGDTGY

AQKFQG KATL TADKSSKTVY MELSSLASED SAVYYCAR GD YYGSNSLDY W GQGTSVTVSS

ASTKGPSVFP  LAPSSKSTSG GTAALGCLVK DYFPEPVTVS WNSGALTSGV HTFPAVLQSS

GLYSLSSVVT  VPSSSLGTQT YICNVNHKPS NTKVDKKVEP KSCDKTHTCP PCPAPELLGG

PSVFLFPPKP  KDTLMISRTP EVTCVVVDVS HEDPEVKFNW YVDGVEVHNA KTKPREEQYN

STYRVVSVLT  VLHQDWLNGK EYKCKVSNKA LPAPTEKTIS KAKGQPREPQ VYTLPPSRDE

LTKNQVSLTC  LVKGFYPSDI AVEWESNGQP ENNYKTTPPV LDSDGSFFLY SKLTVDKSRW

QQGNVFSCSV  MHEALHNHYT QKSLSLSPGK (SEQ ID NO: 12)
DIVMTQSHLS MSTSLGDPVS ITC KASQDVS TVVA WYQQKP GQSPRRLIY S ASYRYI GVPD

RFTGSGAGTD FTFTISSVQA EDLAVYYC QQ HYSPPYT FGG GTKLEIK RTV AAPSVFIFPP

SDEQLKSGTA  SVVCLLNNFY PREAKVQWKV DNALQSGNSQ ESVTEQDSKD STYSLSSTLT

LSKADYEKHK  VYACEVTHQG LSSPVTKSFN RGEC
```

In some embodiments, the anti-CD38 antibody or antigen-binding fragment competes for binding to CD38 with, or binds to the same epitope on CD38 as, Ab2.

In some embodiments, the anti-CD38 antibody has a heavy chain that comprises:

a) heavy chain CDR1-3 (HCDR1-3) that comprise the amino acid sequences of SEQ ID NOs: 15-17, respectively;

c) a V$_H$ that comprises the amino acid sequence of SEQ ID NO: 13 and a V$_L$ that comprises the amino acid sequence of SEQ ID NO: 14; and d) an HC that comprises the amino acid sequence of SEQ ID NO: 11 and an LC that comprises the amino acid sequence of SEQ ID NO: 12.

In certain embodiments, the anti-CD38 antibody is antibody Ab3, or a variant thereof, wherein the variant may for example contain certain minimum amino acid changes relative to Ab3 (e.g., 1, 2, 3, 4, 5, 6, 7, 8, 9, or 10 amino acid changes, which may be, e.g., in the framework regions) without losing the antigen-binding specificity of the antibody.

The heavy and light chain amino acid sequences of Ab3 are SEQ ID NOs: 25 and 26, respectively. These two sequences are shown below. Variable domains are italicized. CDRs are shown in boxes.

c) a $V_L$ that comprises the amino acid sequence of SEQ ID NO: 28; or d) the amino acid sequence of SEQ ID NO: 26.

In some embodiments, an anti-CD38 antibody described herein comprises any of the above heavy chains in combination with any of the above light chains.

In some embodiments, an anti-CD38 antibody described herein comprises:

```
                                                             (SEQ ID NO: 25)
QVQLVQSGAE VVKPGASVKV SCKAS GYTFT SYA MHWVKEA PGQRLEWIGY IYPGQGGT NY

NQKFQGRATL TADTSASTAY MELSSLRSED TAVYFC ARTG GLRRAYFTY W GQGTLVTVSS

ASTKGPSVFP  LAPSSKSTSG GTAALGCLVK DYFPEPVTVS WNSGALTSGV HTFPAVLQSS

GLYSLSSVVT  VPSSSLGTQT YICNVNHKPS NTKVDKKVEP KSCDKTHTCP PCPAPELLAG

PDVFLFPPKP  KDTLMISRTP EVTCVVVDVS HEDPEVKFNW YVDGVEVHNA KTKPREEQYN

STYRVVSVLT  VLHQDWLNGK EYKCKVSNKA LPLPEEKTIS KAKGQPREPQ VYTLPPSRDE

LTKNQVSLTC  LVKGFYPSDI AVEWESNGQP ENNYKTTPPV LDSDGSFFLY SKLTVDKSRW

QQGNVFSCSV  MHEALHNHYT QKSLSLSPG (SEQ ID NO: 26)
DIVLTQSPAT LSLSPGERAT ISCRAS QSVS SYGQGF MHWY QQKPGQPPRL LIY GAS SRAT

GIPARFSGSG SGTDFTLTIS PLEPEDFAVY YC QQNKEDPW T FGGGTKLEI KRTVAAPSVF

IFPPSDEQLK  SGTASVVCLL NNFYPREAKV QWKVDNALQS GNSQESVTEQ DSKDSTYSLS

STLTLSKADY  EKHKVYACEV THQGLSSPVT KSFNRGEC
```

In some embodiments, the anti-CD38 antibody or antigen-binding fragment competes for binding to CD38 with, or binds to the same epitope on CD38 as, Ab3.

In some embodiments, the anti-CD38 antibody has a heavy chain that comprises:
a) heavy chain CDR1-3 (HCDR1-3) that comprise the amino acid sequences of SEQ ID NOs: 29-31, respectively;
b) a heavy chain variable domain ($V_H$) that is at least 75%, 80%, 85%, 90%, 91%, 92%, 93%, 94%, 95%, 96%, 97%, 98%, or 99% identical in sequence to the amino acid sequence of SEQ ID NO: 27;
c) a $V_H$ that comprises the amino acid sequence of SEQ ID NO: 27; or
d) the amino acid sequence of SEQ ID NO: 25.

In some embodiments, the anti-CD38 antibody has a light chain that comprises:
a) light chain CDR1-3 (LCDR1-3) that comprise the amino acid sequences of SEQ ID NOs: 32-34, respectively;
b) a light chain variable domain ($V_L$) that is at least 75%, 80%, 85%, 90%, 91%, 92%, 93%, 94%, 95%, 96%, 97%, 98%, or 99% identical in sequence to the amino acid sequence of SEQ ID NO: 28;

a) HCDR1-3 and LCDR1-3 that comprise the amino acid sequences of SEQ ID NOs: 29-34, respectively;
b) a $V_H$ that is at least 75%, 80%, 85%, 90%, 91%, 92%, 93%, 94%, 95%, 96%, 97%, 98%, or 99% identical in sequence to the amino acid sequence of SEQ ID NO: 27 and a $V_L$ that is at least 75%, 80%, 85%, 90%, 91%, 92%, 93%, 94%, 95%, 96%, 97%, 98%, or 99% identical in sequence to the amino acid sequence of SEQ ID NO: 28;
c) a $V_H$ that comprises the amino acid sequence of SEQ ID NO: 27 and a $V_L$ that comprises the amino acid sequence of SEQ ID NO: 28; and
d) an HC that comprises the amino acid sequence of SEQ ID NO: 25 and an LC that comprises the amino acid sequence of SEQ ID NO: 26.

In certain embodiments, the anti-CD38 antibody is antibody Ab4, or a variant thereof, wherein the variant may for example contain certain minimum amino acid changes relative to Ab4 (e.g., 1, 2, 3, 4, 5, 6, 7, 8, 9, or 10 amino acid changes, which may be, e.g., in the framework regions) without losing the antigen-binding specificity of the antibody.

The heavy and light chain amino acid sequences of Ab4 are SEQ ID NOs: 35 and 36, respectively. These two sequences are shown below. Variable domains are italicized. CDRs are shown in boxes.

```
                                                             (SEQ ID NO: 35)
QVQLVESGGG VVQPGRSLRL SCAAS GFTFS SYG MHWVRQA PGKGLEWVAV IWYDGSNK YY

ADSVKGRFTI SGDNSKNTLY LQMNSLRAED TAVYYC ARMF RGAFDY WGQG TLVTVSSAST
```

```
                            -continued
KGPSVFPLAP    SSKSTSGGTA ALGCLVKDYF PEPVTVSWNS GALTSGVHTF PAVLQSSGLY

SLSSVVTVPS    SSLGTQTYIC NVNHKPSNTK VDKKVEPKSC DKTHTCPPCP APELLAGPDV

FLFPPKPKDT    LMISRTPEVT CVVVDVSHED PEVKFNWYVD GVEVHNAKTK PREEQYNSTY

RVVSVLTVLH    QDWLNGKEYK CKVSNKALPL PEEKTISKAK GQPREPQVYT LPPSRDELTK

NQVSLTCLVK    GFYPSDIAVE WESNGQPENN YKTTPPVLDS DGSFFLYSKL TVDKSRWQQG

NVFSCSVMHE    ALHNHYTQKS LSLSPG (SEQ ID NO: 36)
AIQMTQSPSS    LSASVGDRVT ITCRAS QGIR ND LGWYQQKP GKAPKLLIY A AS SLQSGVPS

RFSGSGSGTD    FTLTISGLQP EDSATYYC LQ DYIYYPT FGQ GTKVEIKRTV AAPSVFIFPP

SDEQLKSGTA    SVVCLLNNFY PREAKVQWKV DNALQSGNSQ ESVTEQDSKD STYSLSSTLT

LSKADYEKHK    VYACEVTHQG LSSPVTKSFN RGEC
```

In some embodiments, the anti-CD38 antibody or antigen-binding fragment competes for binding to CD38 with, or binds to the same epitope on CD38 as, Ab4.

In some embodiments, the anti-CD38 antibody has a heavy chain that comprises:

a) heavy chain CDR1-3 (HCDR1-3) that comprise the amino acid sequences of SEQ ID NOs: 39-41, respectively;

b) a heavy chain variable domain ($V_H$) that is at least 75%, 80%, 85%, 90%, 91%, 92%, 93%, 94%, 95%, 96%, 97%, 98%, or 99% identical in sequence to the amino acid sequence of SEQ ID NO: 37;

c) a $V_H$ that comprises the amino acid sequence of SEQ ID NO: 37; or d) the amino acid sequence of SEQ ID NO: 35.

In some embodiments, the anti-CD38 antibody has a light chain that comprises:

a) light chain CDR1-3 (LCDR1-3) that comprise the amino acid sequences of SEQ ID NOs: 42-44, respectively;

b) a light chain variable domain ($V_L$) that is at least 75%, 80%, 85%, 90%, 91%, 92%, 93%, 94%, 95%, 96%, 97%, 98%, or 99% identical in sequence to the amino acid sequence of SEQ ID NO: 38;

c) a $V_L$ that comprises the amino acid sequence of SEQ ID NO: 38; or d) the amino acid sequence of SEQ ID NO: 36.

In some embodiments, an anti-CD38 antibody described herein comprises any of the above heavy chains in combination with any of the above light chains.

In some embodiments, an anti-CD38 antibody described herein comprises:

a) HCDR1-3 and LCDR1-3 that comprise the amino acid sequences of SEQ ID NOs: 39-44, respectively;

b) a $V_H$ that is at least 75%, 80%, 85%, 90%, 91%, 92%, 93%, 94%, 95%, 96%, 97%, 98%, or 99% identical in sequence to the amino acid sequence of SEQ ID NO: 37 and a $V_L$ that is at least 75%, 80%, 85%, 90%, 91%, 92%, 93%, 94%, 95%, 96%, 97%, 98%, or 99% identical in sequence to the amino acid sequence of SEQ ID NO: 38;

c) a $V_H$ that comprises the amino acid sequence of SEQ ID NO: 37 and a $V_L$ that comprises the amino acid sequence of SEQ ID NO: 38; and d) an HC that comprises the amino acid sequence of SEQ ID NO: 35 and an LC that comprises the amino acid sequence of SEQ ID NO: 36.

In some embodiments, an anti-CD38 antibody described herein has a human IgG$_1$ constant region.

In some embodiments, an anti-CD38 antibody described herein has a human immunoglobulin kappa light chain region.

In some embodiments, an anti-CD38 antibody or antigen-binding fragment described herein binds CD38 with a K$_D$ of $1\times10^{-8}$ M or lower, e.g., $9\times10^{-9}$ M, $8\times10^{-9}$ M, $7\times10^{-9}$ M, $6\times10^{-9}$ M, $5\times10^{-9}$ M, $4\times10^{-9}$ M, $3\times10^{-9}$ M, $2\times10^{-9}$ M, or $1\times10^{-9}$ M. In certain embodiments, the anti-CD38 antibody or antigen-binding fragment binds CD38 with a K$_D$ of $3\times10^{-9}$ M or lower.

In some embodiments, an anti-CD38 antibody or antigen-binding fragment described herein kills a CD38-positive cell by apoptosis, ADCC, and CDC; in certain embodiments, killing said CD38-positive cells by apoptosis can occur in the absence of stroma cells or stroma-derived cytokines. In some embodiments, the CD38-positive cell is a malignant cell. In some embodiments, the CD38-positive cell is a B cell. In certain embodiments, the CD38-positive cell is a tumor cell derived from a hematopoietic malignancy. In a more preferred embodiment, the CD38-positive cell is a lymphoma cell, a leukemia cell, or a multiple myeloma cell. In a further preferred embodiment, the CD38-positive cell is a NHL, BL, MM, B-CLL, ALL, TCL, AML, HCL, HL, or CML cell.

In some embodiments, an anti-CD38 antibody or antigen-binding fragment described herein is capable of killing at least 10%, 15%, 20%, 21%, 22%, 23%, 24%, 25%, 26%, 27%, 28%, 29%, 30%, 35%, or 40% (e.g., at least 24%) of Daudi lymphoma cells in the absence of stroma cells or stroma-derived cytokines in vitro.

In some embodiments, an anti-CD38 antibody or antigen-binding fragment described herein is capable of killing at least 3%, 4%, 5%, 6%, 7%, 8%, 9%, or 10% (e.g., at least 7%) of Ramos lymphoma cells in the absence of stroma cells or stroma-derived cytokines in vitro.

In some embodiments, an anti-CD38 antibody or antigen-binding fragment described herein is capable of killing at least 5%, 6%, 7%, 8%, 9%, 10%, 11%, 12%, 13%, 14%, 15%, 16%, 17%, 18%, 19%, or 20% (e.g., at least 11%) of MOLP-8 multiple myeloma cells in the absence of stroma cells or stroma-derived cytokines in vitro.

In some embodiments, an anti-CD38 antibody or antigen-binding fragment described herein is capable of killing at least 25%, 30%, 31%, 32%, 33%, 34%, 35%, 36%, 37%, 38%, 39%, 40%, 45%, or 50% (e.g., at least 36%) of SU-DHL-8 lymphoma cells in the absence of stroma cells or stroma-derived cytokines in vitro.

In some embodiments, an anti-CD38 antibody or antigen-binding fragment described herein is capable of killing at least 20%, 25%, 26%, 27%, 28%, 29%, 30%, or 35% (e.g., at least 27%) of NU-DUL-1 lymphoma cells in the absence of stroma cells or stroma-derived cytokines in vitro.

In some embodiments, an anti-CD38 antibody or antigen-binding fragment described herein is capable of killing at least 50%, 55%, 60%, 61%, 62%, 63%, 64%, 65%, 70%, or 75% (e.g., at least 62%) of DND-41 leukemia cells in the absence of stroma cells or stroma-derived cytokines in vitro.

In some embodiments, an anti-CD38 antibody or antigen-binding fragment described herein is capable of killing at least 5%, 6%, 7%, 8%, 9%, 10%, 11%, 12%, or 13% (e.g., at least 9%) of JVM-13 leukemia cells in the absence of stroma cells or stroma-derived cytokines in vitro.

In some embodiments, an anti-CD38 antibody or antigen-binding fragment described herein is capable of killing at least 1%, 2%, 3%, 4%, 5%, 6%, 7%, or 8% (e.g., at least 4%) of HC-1 leukemia cells in the absence of stroma cells or stroma-derived cytokines in vitro.

In some embodiments, the agent that specifically binds to CD38 is a conjugate comprising an anti-CD38 antibody or antigen-binding fragment described herein linked to a cytotoxic agent. The cytotoxic agent may be selected from, e.g., a maytansinoid, a small drug, a tomaymycin derivative, a leptomycin derivative, a prodrug, a taxoid, CC-1065 and a CC-1065 analog, or any cytotoxic agent described in U.S. Pat. No. 8,153,765 (which is incorporated by reference in its entirety herein).

The class of an anti-TGF-β or anti-CD38 antibody described herein may be changed or switched with another class or subclass. In one aspect, a nucleic acid molecule encoding $V_L$ or $V_H$ is isolated using methods well-known in the art such that it does not include nucleic acid sequences encoding CL or CH. The nucleic acid molecules encoding $V_L$ or $V_H$ then are operatively linked to a nucleic acid sequence encoding a CL or CH, respectively, from a different class of immunoglobulin molecule. This may be achieved using a vector or nucleic acid molecule that comprises a CL or CH chain, as described above. For example, an antibody that was originally IgM may be class switched to IgG. Further, the class switching may be used to convert one IgG subclass to another, e.g., from IgG1 to IgG2. A κ light chain constant region can be changed, e.g., to a λ light chain constant region. A preferred method for producing an antibody as described herein with a desired Ig isotype comprises the steps of isolating a nucleic acid molecule encoding the heavy chain of an antibody and a nucleic acid molecule encoding the light chain of an antibody, obtaining the variable domain of the heavy chain, ligating the variable domain of the heavy chain with the constant region of a heavy chain of the desired isotype, expressing the light chain and the ligated heavy chain in a cell, and collecting the antibody with the desired isotype.

An antibody described herein can be an IgG, an IgM, an IgE, an IgA, or an IgD molecule, but is typically of the IgG isotype, e.g. of IgG subclass $IgG_1$, $IgG_{2a}$, or $IgG_{2b}$, $IgG_3$, or $IgG_4$.

In one embodiment, the antibody may comprise at least one mutation in the Fc region. A number of different Fc mutations are known, where these mutations provide altered effector function. For example, in many cases it will be desirable to reduce or eliminate effector function, e.g., where ligand/receptor interactions are undesired or in the case of antibody-drug conjugates.

In some embodiments, the antibodies described herein, such as the anti-TGF-β and anti-CD38 antibodies, do not have the C-terminal lysine in the heavy chain. The C-terminal lysine may be removed during manufacture or by recombinant technology (i.e., the coding sequence of the heavy chain does not include a codon for the C-terminal terminal lysine). Thus, contemplated within the present disclosure also are antibodies comprising the heavy chain amino acid sequence of SEQ ID NO: 1 or 11 without the C-terminal lysine.

Combination Therapies

The present disclosure provides a combination therapy that comprises an agent that specifically binds to human TGF-β and an agent that specifically binds to human CD38. In some embodiments, the agent that specifically binds to TGF-β may be any of the anti-TGF-β antibodies or antigen-binding fragments thereof described herein. In some embodiments, the agent that specifically binds to CD38 may be any of the anti-CD38 antibodies or antigen-binding fragments thereof described herein. The present disclosure also contemplates combination therapy with one or more other agents that inhibit TGF-β (e.g., galunisertib, LY3200882, PF-06952229 (Pfizer), GFH-018 (GenFleet), and/or vactosertib) and/or one or more other agents that inhibit CD38. A combination therapy described herein may take the form of a method for treatment using said agents or a pharmaceutical composition comprising said agents.

The present disclosure also contemplates a combination therapy that comprises an agent that specifically binds to human CD38 (e.g., an anti-CD38 antibody or antigen-binding fragment thereof, such as one described herein) and an agent that specifically binds to LAP (e.g., an anti-LAP antibody).

In some embodiments, the combination therapy of the present disclosure uses anti-TGF-β antibody Ab1 and anti-CD38 antibody Ab2. In some embodiments, the combination therapy of the present disclosure uses an antibody or an antigen-binding fragment thereof that competes for binding or binds to the same epitope of TGF-β as Ab1 and an antibody that competes for binding or binds to the same epitope of CD38 as Ab2. In certain embodiments, the Ab1 and Ab2 agents are used in separate compositions (e.g., administered sequentially). In certain embodiments, the Ab1 and Ab2 agents are used in a single composition.

In certain embodiments, the combination therapy of the present disclosure uses:

an anti-TGF-β antibody or an antigen-binding fragment thereof comprising HCDR1-3 and LCDR1-3 with the amino acid sequences of SEQ ID NOs: 5-10, respectively; and an anti-CD38 antibody comprising HCDR1-3 and LCDR1-3 with the amino acid sequences of SEQ ID NOs: 15-20, respectively;

an anti-TGF-β antibody or an antigen-binding fragment thereof comprising a $V_H$ at least 75%, 80%, 85%, 90%, 91%, 92%, 93%, 94%, 95%, 96%, 97%, 98%, or 99% identical in sequence to the amino acid sequence of SEQ ID NO: 3, and a $V_L$ at least 75%, 80%, 85%, 90%, 91%, 92%, 93%, 94%, 95%, 96%, 97%, 98%, or 99% identical in sequence to the amino acid sequence of SEQ ID NO: 4; and an anti-CD38 antibody comprising a $V_H$ at least 75%, 80%, 85%, 90%, 91%, 92%, 93%, 94%, 95%, 96%, 97%, 98%, or 99% identical in sequence to the amino acid sequence of SEQ ID NO: 13, and a $V_L$ at least 75%, 80%, 85%, 90%, 91%, 92%, 93%, 94%, 95%, 96%, 97%, 98%, or 99% identical in sequence to the amino acid sequence of SEQ ID NO: 14;

an anti-TGF-β antibody or an antigen-binding fragment thereof comprising a $V_H$ and $V_L$ with the amino acid sequences of SEQ ID NOs: 3 and 4, respectively; and an anti-CD38 antibody comprising a $V_H$ and $V_L$ with the amino acid sequences of SEQ ID NOs: 13 and 14, respectively; or an anti-TGF-β antibody comprising an HC and LC with the amino acid sequences of SEQ ID NOs: 1 and 2, respectively; and an anti-CD38 antibody comprising an HC and LC with the amino acid sequences of SEQ ID NOs: 11 and 12, respectively.

In some embodiments, the anti-TGF-β and anti-CD38 antibodies used in the combination therapy have isotypes $IgG_4$ and $IgG_1$, respectively. In certain embodiments, the anti-TGF-β antibody has a human $IgG_4$ constant region where residue 228 (EU numbering) in the hinge region has been mutated from serine to proline.

In some embodiments, an anti-TGF-β antibody or antigen-binding fragment thereof described herein relieves the immunosuppressive effects of TGF-β on NK cell-mediated ADCC by an anti-CD38 antibody described herein, rendering the combination therapy of the present disclosure more effective than treatment with the anti-CD38 antibody alone.

In some embodiments, a combination therapy comprising an agent that specifically binds to human TGF-β and an agent that specifically binds to human CD38 (e.g., an anti-TGF-β antibody and an anti-CD38 antibody, such as Ab1 and Ab2, respectively) may further comprise an additional agent or therapy. In certain embodiments, the additional agent or therapy may be, e.g., lenalidomide, pomalidomide, bortezomib, methylprednisolone, dexamethasone, prednisone, melphalan, bortezomib, ixazomib, carfilzomib, thalidomide, cyclophosphamide, pembrolizumab, a pan-histone deacetylase inhibitor (e.g., Panobinostat), a retinoic acid (e.g., all-trans retinoic acid), radioimmunotherapy, chemotherapy, etc. In certain embodiments, the additional agent or therapy is a combination of lenalidomide and dexamethasone. In certain embodiments, the additional agent or therapy is a combination of bortezomib, melphalan, and prednisone. In certain embodiments, the additional agent or therapy is a combination of bortezomib and dexamethasone. In certain embodiments, the additional agent or therapy is a combination of pomalidomide and dexamethasone. In certain embodiments, the additional agent or therapy is dexamethasone. In some embodiments, the additional agent or therapy is a treatment for the condition targeted by the combination therapy of the present disclosure. For example, where the condition is myeloma (e.g., multiple myeloma), the treatment may be, e.g., elotuzumab.

In some embodiments, the agents in a combination therapy of the present disclosure are administered in more than one composition. In certain embodiments, each agent is provided in a separate composition. In a case where there is more than one composition, the compositions can be administered simultaneously, sequentially, or separately. In other embodiments, the agents are administered in a single composition. For example, a combination therapy comprising an anti-TGF-β antibody and an anti-CD38 antibody may involve administration of a single composition comprising both antibodies, or a separate composition for each antibody (wherein the separate compositions may be administered sequentially or concurrently).

Therapeutic Uses of Combination Therapies of the Present Disclosure

In one aspect, the combination therapies of the present disclosure are used to treat a condition that relies on CD38 expression. In some embodiments, the combination therapies of the present disclosure are used to treat a hyperproliferative disorder, an inflammatory disease, an autoimmune disease, or a fibrotic condition. In certain embodiments, the combination therapies of the present disclosure are used to treat cancer.

In some embodiments, the combination therapies of the present disclosure target CD38-positive cells (e.g., CD38-positive cancer cells such as malignant B cells). A cell may be identified as CD38-positive by any suitable method for determining gene or protein expression, for example, by histology, flow cytometry, RT-PCR, or RNA-Seq. Cancer cells used for the determination may be obtained through tumor biopsy or through collection of circulating tumor cells. Without wishing to be bound by theory, it is contemplated that the agent that specifically binds to CD38 will bind to CD38-positive cells and mediate ADCC/CDC on the cells, and that the agent that specifically binds to TGF-β will reduce the immunosuppressive effect of TGF-β, thus enhancing the efficacy of the cancer therapy.

In some embodiments, the combination therapies of the present disclosure are used to treat myeloma such as multiple myeloma (e.g., relapsed and/or refractory multiple myeloma, newly diagnosed multiple myeloma (optionally not eligible for transplant), smoldering multiple myeloma, light chain myeloma, non-secretory myeloma, immunoglobulin D myeloma, or immunoglobulin E myeloma). In certain embodiments, the combination therapies of the present disclosure result in less bone destruction in myeloma bone lesions than therapy with only an agent that binds specifically to CD38 (e.g., an anti-CD38 antibody). In particular embodiments, the combination therapies of the present disclosure may result in improved healing of myeloma bone lesions. Without wishing to be bound by theory, it is contemplated that the agent that specifically binds to TGF-β (e.g., an anti-TGF-β antibody) will inhibit suppressive activity of TGF-beta on osteoblast differentiation and matrix mineralization, thus enhancing bone formation and resulting in bone remodeling and bone healing. Further, because mature osteoblasts enhance apoptosis and cell cycle arrest of multiple myeloma cells, the agent that specifically binds to TGF-β may also suppress multiple myeloma cell growth.

In some embodiments, the combination therapies of the present disclosure are used to treat, e.g., amyloidosis (such as relapsed or refractory primary amyloidosis or light chain amyloidosis), myelodysplastic syndrome (MDS), monoclonal gammopathy, solitary plasmacytoma, extramedullary plasmacytoma, or Waldenström macroglobulinemia.

In some embodiments, the combination therapies of the present disclosure are used to treat a hematological malignancy, e.g., leukemia or lymphoma. For example, the malignancy may be chronic lymphocytic leukemia, B and T acute lymphocytic leukemia, acute lymphoblastic leukemia (e.g., B cell acute lymphoblastic leukemia or B cell or T cell precursor acute lymphoblastic leukemia), chronic lymphocytic acute myeloid leukemia, chronic myeloid leukemia, acute myelogenous leukemia, chronic myelogenous leukemia, promyelocytic leukemia, and hairy cell leukemia), non-Hodgkin's lymphoma, Hodgkin's lymphoma, Burkitt's lymphoma, B cell lymphoma (such as diffuse large B-cell lymphoma or germinal center B-cell lymphoma), T cell lymphoma (such as peripheral T-cell lymphoma), natural killer/T cell lymphoma (e.g., nasal type), lymphoblastic lymphoma, mantle cell lymphoma, and follicular lymphoma. In certain embodiments, the combination therapies of the present disclosure are used to treat lymphoblastic leukemia.

Other cancers that may be treated by the combination therapies of the present disclosure may be solid tumors and may include, but are not limited to, skin cancer (e.g., melanoma, including unresectable or metastatic melanoma, cutaneous squamous cell carcinoma, xeroderma pigmentosa, and keratoacanthoma), thyroid cancer, lung cancer (e.g., non-small cell lung cancer), esophageal cancer, stomach cancer, colon cancer, colorectal cancer, pancreatic cancer, liver cancer (e.g., hepatocellular carcinoma), primary peritoneal cancer, bladder cancer, renal cancer or kidney cancer (e.g., renal cell carcinoma), urothelial carcinoma, breast cancer (e.g., Her2-positive breast cancer or triple negative breast cancer), ovarian cancer, fallopian cancer, cervical cancer, uterine cancer, prostate cancer, testicular cancer, head and neck cancer (e.g., head and neck squamous cell carcinoma), brain cancer, neuroblastoma, glioblastoma, glioma, astrocytoma, schwannoma, mesothelioma, fibrosarcoma, rhabdomyosarcoma, osteosarcoma, Kaposi's sarcoma, seminoma, and teratocarinoma. In some embodiments, a combination therapy of the present disclosure is used to treat non-small cell lung cancer, prostate cancer (e.g., prostate adenocarcinoma), glioblastoma, hepatocellular cancer, ovarian cancer, head and neck cancer, urothelial cancer, or colorectal cancer.

The combination therapies of the present disclosure can also be useful to inhibit cyclosporine-mediated malignancy or cancer progression (e.g., metastases).

In some embodiments, the combination therapies of the present disclosure are useful in treating cancer at an early, intermediate, advanced, or metastatic stage. In some embodiments, the combination therapies are used to treat a patient (e.g., a multiple myeloma patient) who has received at least one prior therapy. In some embodiments, the combination therapies are useful in treating relapsed or refractory cancer.

In some embodiments, the combination therapies of the present disclosure are used to treat any of the conditions described herein (e.g., a cancer described herein) in a patient who has progressed on or after standard therapy for said condition, or for whom there is no effective standard therapy for said condition.

In some embodiments, the combination therapies of the present disclosure are used to treat any of the conditions described herein (e.g., a cancer described herein) in a patient who is resistant to one or more standard therapies for said condition. In certain embodiments, the patient may have a condition (e.g., a cancer such as multiple myeloma) refractory to treatment with Ab2, Ab3, Ab4, galunisertib, LY3200882, XOMA 089, daratumumab, MOR202, TAK-079, TAK-573, TAK-169, HexaBody®-CD38, or any combination thereof. The condition may be refractory to treatment with an agent that specifically binds to CD38. In particular embodiments, the patient may have a condition (e.g., a cancer such as multiple myeloma) refractory to treatment with Ab2 or treatment with daratumumab, or refractory to both treatments.

In some embodiments, the combination therapies of the present disclosure are used to treat a cancer described herein, wherein the cancer shows high levels of TGF-β expression.

In certain embodiments, the cancer shows high levels of TGF-β expression and is resistant to treatment with an agent that specifically binds to CD38 (e.g., Ab2, Ab3, Ab4, daratumumab, MOR202, TAK-079, TAK-573, TAK-169, HexaBody®-CD38, or any combination thereof). In particular embodiments, the cancer may be refractory to treatment with Ab2 or treatment with daratumumab, or refractory to both treatments.

In some embodiments, the combination therapies of the present disclosure are used to treat a patient with newly diagnosed multiple myeloma who cannot receive a type of stem cell transplant that uses their own stem cells (autologous stem cell transplant). Additionally or alternatively, the patient has received at least one prior medicine to treat multiple myeloma. In particular embodiments, the combination therapies further comprise:

a) lenalidomide and/or dexamethasone, b) bortezomib, lenalidomide, and/or dexamethasone, c) bortezomib, melphalan, and/or prednisone, or d) bortezomib and/or dexamethasone.

In some embodiments, the combination therapies of the present disclosure are used to treat a patient who has received at least two prior medicines to treat multiple myeloma. In certain embodiments, the two prior medicines include lenalidomide and/or a proteasome inhibitor.

In some embodiments, the combination therapies of the present disclosure are used to treat a patient who has received at least three prior medicines to treat multiple myeloma. In certain embodiments, the three prior medicines include a proteasome inhibitor and/or an immunomodulatory agent.

In some embodiments, the combination therapies of the present disclosure are used to treat a patient who did not respond to a proteasome inhibitor and/or an immunomodulatory agent.

In some embodiments, the combination therapies of the present disclosure are used to treat a patient with relapsed/refractory multiple myeloma in combination with pomalidomide and/or dexamethasone (e.g., low-dose dexamethasone). In certain embodiments, the patient has received at least two prior medicines to treat multiple myeloma. In particular embodiments, the two prior medicines include lenalidomide and/or a proteasome inhibitor.

"Treat", "treating" and "treatment" refer to a method of alleviating or abrogating a biological disorder and/or at least one of its attendant symptoms. As used herein, to "alleviate" a disease, disorder or condition means reducing the severity and/or occurrence frequency of the symptoms of the disease, disorder, or condition. Further, references herein to "treatment" include references to curative, palliative and prophylactic treatment. It will of course be appreciated that in the context of cancer therapy, "treatment" includes any medical intervention resulting in the slowing of cancer growth, delay in cancer progression or recurrence, or reduction in cancer metastases, as well as partial remission of the cancer in order to prolong life expectancy of a patient.

As used herein, the terms "co-administration", "co-administered" and "in combination with" refer to, without limitation, (i) simultaneous administration of the therapeutic agents to a patient in need of treatment, when such agents are formulated together into a single dosage form, (ii) substantially simultaneous administration of such agents to a patient in need of treatment, when such agents are formulated apart from each other into separate dosage forms, and (iii) sequential administration of such agents to a patient in need of treatment, when such agents are formulated apart from each other into separate dosage forms which are taken at separate times by said patient.

The ratio between the agent that specifically binds to TGF-β (e.g., an anti-TGF-β antibody) and the agent that specifically binds to CD38 (e.g., an anti-CD38 antibody) may be such that the agents are administered in equal amounts (i.e., at 1:1 ratio), but this need not be the case. Depending on the characteristics of the individual agents, it may be desirable to use non-equal amounts of the agents.

It is understood that the combination therapies of the present disclosure may be used in a method of treatment as described herein, may be for use in a treatment as described herein, and/or may be for use in the manufacture of a medicament for a treatment as described herein.

Dosing Regimen

The combination therapies of the present disclosure will be administered in an effective amount for treatment of the condition in question, i.e., at dosages and for periods of time necessary to achieve a desired result. A therapeutically effective amount may vary according to factors such as the particular condition being treated, the age, sex, health, and weight of the patient, and whether the agents are being administered as a stand-alone treatment or in combination with one or more additional anti-cancer treatments.

"Therapeutically effective amount" refers to the amount of the therapeutic agent being administered that will relieve to some extent one or more of the symptoms of the disorder being treated. This amount can be determined by a health-care professional using well established principles. A therapeutically effective amount of an anti-cancer therapeutic may, for example, result in tumor shrinkage, increased survival, elimination of cancer cells, decreased disease progression, reversal of metastasis, or other clinical endpoints desired by healthcare professionals.

In some embodiments, patients are monitored for cardiac and pulmonary side effects when being treated with the combination therapies of the present disclosure.

Host Cells and Methods of Antibody and Antibody Composition Production

One aspect of the present disclosure relates to methods for producing the antibodies for the present combination therapies. One embodiment relates to a method for producing antibodies as described herein, comprising providing recombinant host cells capable of expressing the antibodies, culturing said host cells under conditions suitable for expression of the antibodies, and isolating the resulting antibodies. Antibodies produced by such expression in such recombinant host cells are referred to herein as "recombinant antibodies." Also described are progeny cells of such host cells, and antibodies produced by same.

The term "recombinant host cell" (or simply "host cell"), as used herein, means a cell into which a recombinant expression vector has been introduced. The host cell may comprise, e.g., one or more vectors as described herein. The host cells may comprise, e.g., a nucleotide sequence encoding the heavy chain or an antigen-binding fragment thereof, a nucleotide sequence encoding the light chain or an antigen-binding fragment thereof, or both, of an anti-TGF-β and/or anti-CD38 antibody or antigen-binding fragment thereof described herein. It should be understood that "recombinant host cell" and "host cell" mean not only the particular subject cell but also the progeny of such a cell. Because certain modifications may occur in succeeding generations due to either mutation or environmental influences, such progeny may not, in fact, be identical to the parent cell, but are still included within the scope of the term "host cell" as used herein.

In some embodiments, a host cell of the present disclosure comprises:

a nucleotide sequence that encodes the heavy chain or an antigen-binding fragment thereof, a nucleotide sequence that encodes the light chain or an antigen-binding fragment thereof, or both, of an anti-TGF-β antibody as described herein, and a nucleotide sequence that encodes the heavy chain or an antigen-binding fragment thereof, a nucleotide sequence that encodes the light chain or an antigen-binding fragment thereof, or both, of an anti-CD38 antibody as described herein.

Nucleic acid molecules encoding heavy and/or light chain amino acid sequences of anti-TGF-β and/or anti-CD38 antibodies or antigen-binding fragments thereof may be comprised in expression vectors. Expression vectors, in which the nucleic acid sequences of interest are linked to necessary expression control sequences such as transcriptional and translational control sequences, include plasmids, retroviruses, adenoviruses, adeno-associated viruses (AAV), plant viruses such as cauliflower mosaic virus, tobacco mosaic virus, cosmids, YACs, EBV derived episomes, and the like. The antibody light chain coding sequence and the antibody heavy chain coding sequence can be inserted into separate vectors, and may be operatively linked to the same or different expression control sequences (e.g., promoters). In one embodiment, both coding sequences are inserted into the same expression vector and may be operatively linked to the same expression control sequences (e.g., a common promoter), to separate identical expression control sequences (e.g., promoters), or to different expression control sequences (e.g., promoters). The antibody coding sequences may be inserted into the expression vector by standard methods (e.g., ligation of complementary restriction sites on the antibody gene fragment and vector, or blunt end ligation if no restriction sites are present).

The expression vectors encoding the antibodies and antigen-binding fragments described herein may be introduced into host cells for expression. In some embodiments, the anti-TGF-β antibody-encoding expression vectors and the anti-CD38 antibody-encoding expression vectors are introduced to separate host cells. In other embodiments, the expression vectors are introduced to the same host cell. The host cells are cultured under conditions suitable for expression of the antibody, which is then harvested and isolated. Host cells include mammalian, plant, bacterial or yeast host cells. Mammalian cell lines available as hosts for expression are well known in the art and include many immortalized cell lines available from the American Type Culture Collection (ATCC). These include, inter alia, Chinese hamster ovary (CHO) cells, NS0 cells, SP2 cells, HEK-293T cells, 293 Freestyle cells (Invitrogen), NIH-3T3 cells, HeLa cells, baby hamster kidney (BHK) cells, African green monkey kidney cells (COS), human hepatocellular carcinoma cells (e.g., Hep G2), A549 cells, and a number of other cell lines. Cell lines may be selected based on their expression levels. Other cell lines that may be used are insect cell lines, such as Sf9 or Sf21 cells.

Further, expression of antibodies can be enhanced using a number of known techniques. For example, the glutamine synthetase gene expression system (the GS system) is a common approach for enhancing expression under certain conditions.

Tissue culture media for the host cells may include, or be free of, animal-derived components (ADC), such as bovine serum albumin. In some embodiments, ADC-free culture media is preferred for human safety. Tissue culture can be performed using the fed-batch method, a continuous perfusion method, or any other method appropriate for the host cells and the desired yield.

In some embodiments, the present disclosure relates to a method for producing an antibody composition comprising an anti-TGF-β antibody or an antigen-binding fragment thereof and an anti-CD38 antibody or an antigen-binding fragment thereof, the method comprising:

providing first and second host cells, wherein the first host cell is capable of expressing an anti-TGF-β antibody or an antigen-binding fragment thereof as described herein and the second host cell is capable of expressing an anti-CD38 antibody or an antigen-binding fragment thereof as described herein, cultivating the first and second and host cells under conditions suitable for expression of the anti-TGF-β antibody or antigen-binding fragment thereof and the anti-CD38 antibody or antigen-binding fragment thereof, isolating the resulting antibodies or antigen-binding fragments, and optionally combining the antibodies or antigen-binding fragments to produce an antibody composition.

Pharmaceutical Compositions

Another aspect of the present disclosure is pharmaceutical compositions comprising as active ingredients (e.g., as the sole active ingredients) an agent that specifically binds to human TGF-β (e.g., an anti-TGF-β antibody or an antigen-binding fragment thereof) and an agent that specifically binds to human CD38 (e.g., an anti-CD38 antibody or an antigen-binding fragment thereof). The agent that specifically binds to TGF-β and the agent that specifically binds to CD38 can be co-formulated, e.g., mixed and provided in a single composition. The present disclosure also provides (1) a pharmaceutical composition comprising an agent that specifically binds to human TGF-β, and (2) a pharmaceutical composition comprising an agent that specifically binds to human CD38, wherein the pharmaceutical compositions are used in the same combination therapy.

In some embodiments, the pharmaceutical compositions described herein, when administered in a combination therapy of the present disclosure, are intended for treatment (e.g., amelioration and/or prevention) of a disorder, disease, or condition that improves, or slows down in its progression, by modulation of the activity or expression of TGF-β and CD38. In certain embodiments, the pharmaceutical compositions are intended for treatment (e.g., amelioration and/or prevention) of cancer. In particular embodiments, the cancer is multiple myeloma.

In some embodiments, the pharmaceutical composition of the present disclosure comprises an anti-TGF-β antibody described herein that is less than 1% of half antibody. The half antibody formation may be determined through purity analysis of monoclonal antibody preparations by using, for example, SDS-capillary electrophoresis under non-reducing conditions or non-reducing SDS-PAGE analysis, followed by densitometry, or RP-HPLC (Angal et al., Mol Immunol 30(1):105-8 (1993); Bloom et al., Protein Science 6:407-415 (1997); Schuurman et al., 38(1):1-8 (2001); and Solanos et al., Anal Chem 78:6583-94 (2006)).

Generally, the pharmaceutical compositions described herein are suitable to be administered as a formulation in association with one or more pharmaceutically acceptable excipients, e.g., as described below.

The term "excipient" or "carrier" is used herein to describe any ingredient other than the compound(s) of the present disclosure. The choice of excipients will to a large extent depend on factors such as the particular mode of administration, the effect of the excipient on solubility and stability, and the nature of the dosage form. "Pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In some cases, isotonic agents, for example, sugars, polyalcohols such as mannitol, sorbitol, or sodium chloride will be included in the composition. Additional examples of pharmaceutically acceptable substances are wetting agents or minor amounts of auxiliary substances such as wetting or emulsifying agents, preservatives or buffers, which enhance the shelf life or effectiveness of the antibody. In some embodiments, a pharmaceutical composition of the present disclosure may comprise hyaluronidase (e.g., recombinant human hyaluronidase). In certain embodiments, the pharmaceutical composition comprising hyaluronidase may be for subcutaneous administration.

A pharmaceutical composition of the present disclosure may be prepared, packaged, or provided in bulk, as a single unit dose, or as a plurality of single unit doses. As used herein, a "unit dose" is a discrete amount of the pharmaceutical composition comprising a predetermined amount of the active ingredient(s). The amount of each active ingredient is generally equal to the dosage of the active ingredient which would be administered to a subject or a convenient fraction of such a dosage such as, for example, one-half or one-third of such a dosage.

The pharmaceutical compositions of the present disclosure are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intratumoral, and intrasynovial injection or infusions; and kidney dialytic infusion techniques. Regional perfusion is also contemplated. Preferred embodiments may include the intravenous and the subcutaneous routes.

Formulations of a pharmaceutical composition suitable for parenteral administration typically comprise the active ingredient(s) combined with a pharmaceutically acceptable carrier, such as sterile water or sterile isotonic saline. Such formulations may be prepared, packaged, or provided in a form suitable for bolus administration or for continuous administration. Injectable formulations may be prepared, packaged, or provided in unit dosage form, such as in ampoules or in multi dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient(s) are provided in dry (i.e., powder or granular) form for reconstitution with a suitable vehicle (e.g., sterile pyrogen free water) prior to parenteral administration of the reconstituted composition. Parenteral formulations also include aqueous solutions which may contain excipients such as salts, carbohydrates and buffering agents (e.g., with a pH of from 3 to 9), but, for some applications, they may be more suitably formulated as a sterile non-aqueous solution or as a dried (e.g., lyophilized) form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient(s) in microcrystalline form, or in a liposomal preparation. Formulations for parenteral administration may be formulated to be immediate and/or modified release. Modified release formulations include delayed-, sustained-, pulsed-, controlled-, targeted-, and programmed-release.

Articles of Manufacture and Kits

The present disclosure also provides articles of manufacture comprising an agent that specifically binds to human TGF-β and an agent that specifically binds to human CD38. In some embodiments, an article of manufacture of the present disclosure comprises an anti-TGF-β antibody or an antigen-binding fragment thereof described herein, and an anti-CD38 antibody or an antigen-binding fragment thereof described herein. In certain embodiments, the article of manufacture comprises Ab1 and Ab2. The present disclosure further provides methods for manufacturing said articles.

The present disclosure also provides kits comprising an agent that specifically binds to human TGF-β and an agent that specifically binds to human CD38, as well as instructions for the use of the agents in combination. In some embodiments, a kit of the present disclosure comprises an anti-TGF-β antibody or an antigen-binding fragment thereof described herein, and an anti-CD38 antibody or an antigen-binding fragment thereof described herein. In certain embodiments, the kit comprises Ab1 and Ab2.

Unless otherwise defined herein, scientific and technical terms used in connection with the present disclosure shall have the meanings that are commonly understood by those of ordinary skill in the art. Exemplary methods and materials are described below, although methods and materials similar or equivalent to those described herein can also be used in the practice or testing of the present disclosure. In case of conflict, the present specification, including definitions, will control.

Generally, nomenclature used in connection with, and techniques of, cell and tissue culture, molecular biology, immunology, microbiology, genetics, analytical chemistry, synthetic organic chemistry, medicinal and pharmaceutical chemistry, and protein and nucleic acid chemistry and hybridization described herein are those well-known and commonly used in the art. Enzymatic reactions and purification techniques are performed according to manufacturer's specifications, as commonly accomplished in the art or as described herein.

Further, unless otherwise required by context, singular terms shall include pluralities and plural terms shall include the singular. Throughout this specification and embodiments, the words "have" and "comprise," or variations such as "has," "having," "comprises," or "comprising," will be understood to imply the inclusion of a stated integer or group of integers but not the exclusion of any other integer or group of integers.

All publications and other references mentioned herein are incorporated by reference in their entirety. Although a number of documents are cited herein, this citation does not constitute an admission that any of these documents forms part of the common general knowledge in the art.

EXAMPLES

In order for the present disclosure to be better understood, the following examples are set forth. These examples are for illustration only and are not to be construed as limiting the scope of the present disclosure in any manner.

Example 1: TGF-β is Released by Multiple Myeloma and Lymphoma Cell Lines

JJN3, NCI-H929, RPM18226, LP1, MOLP8, SUDHL-4, DAUDI, OCI-LY19, and SUDHL8 cells were cultured in RPMI 1640 (Invitrogen cat. no. 22400-089) supplemented with 10% fetal calf serum (Invitrogen cat. no. 10082-147).

To quantify TGF-β released by MM and lymphoma cell lines, $1\times10^6$ cells of each cell line were plated in one 96 well tissue culture treated plate in a volume of 100 μL RPMI supplemented with 10% fetal calf serum. The cells were incubated at 37° C. for 1 day, 2 days, or 3 days in a 37° C. humidified incubator containing 5% $CO_2$. After centrifugation for 5 minutes at 250 g, 40 μL of supernatant from each well was collected and the level of total human TGF-β was determined using a MSD 96-well multi-array human TGF-β1 assay kit (Meso Scale Discovery cat. no. K151IUC-1) according to the manufacturer's instructions. Briefly, the samples were activated by acid treatment and subsequently neutralized followed by incubation with the capturing antibody. The antibody was then detected using an ELISA-based method, and the results read on an MSD SECTOR Imager.

Total TGF-β was detected in the supernatants of all MM and lymphoma cell lines at levels over 500 μg/mL, and accumulation over time was observed in most cell lines, particularly in JJN3, RPMI8226 and MOLP8 cells (FIG. 1).

Example 2: TGF-β Reduces the Cytolytic Activity of Human NK Cells and Decreases Ab2-Mediated ADCC Log growth phase NK92V cells (NK92-05 CD16 V/V; Conkwest) were suspended in growth medium (Middle MyeloCult H5100 (Stemcell Technologies cat. no. 05150) supplemented with 100 units/mL human Interleukin-2 (R&D cat. no. 202-IL-010/CF)) and seeded into 10 cm dishes at a density of $0.8\times10^5$ cells per mL. The cells were treated with recombinant human TGF-β at a final concentration of 10 ng/mL for overnight, 24 hours, 48 hours, or 72 hours at 37° C.

MOLP8 cells were cultured in RPMI 1640 (Invitrogen cat. no. 22400-089) supplemented with 20% fetal calf serum (Invitrogen cat. no. 10082-147).

Calcein (AM) (Invitrogen cat. no. C3100MP) labeled MOLP8 target cells and NK92V effector cells were seeded into 96-well plates at a density of $4\times10^4$ target cells (MOLP8) and $1.2\times10^5$ effector cells (NK92V) per well. The cells were treated with Ab2 at a concentration of 0, 0.001, 0.1, or 1 µg/mL, or with an $IgG_1$ control (data not shown), for 1 hour at 37° C. Released calcein florescence from lysed target cells in the supernatants was measured using a multimode plate reader (Envision). The intensity of the fluorescence signal was directly proportional to the number of lysed target cells.

Figure 2:
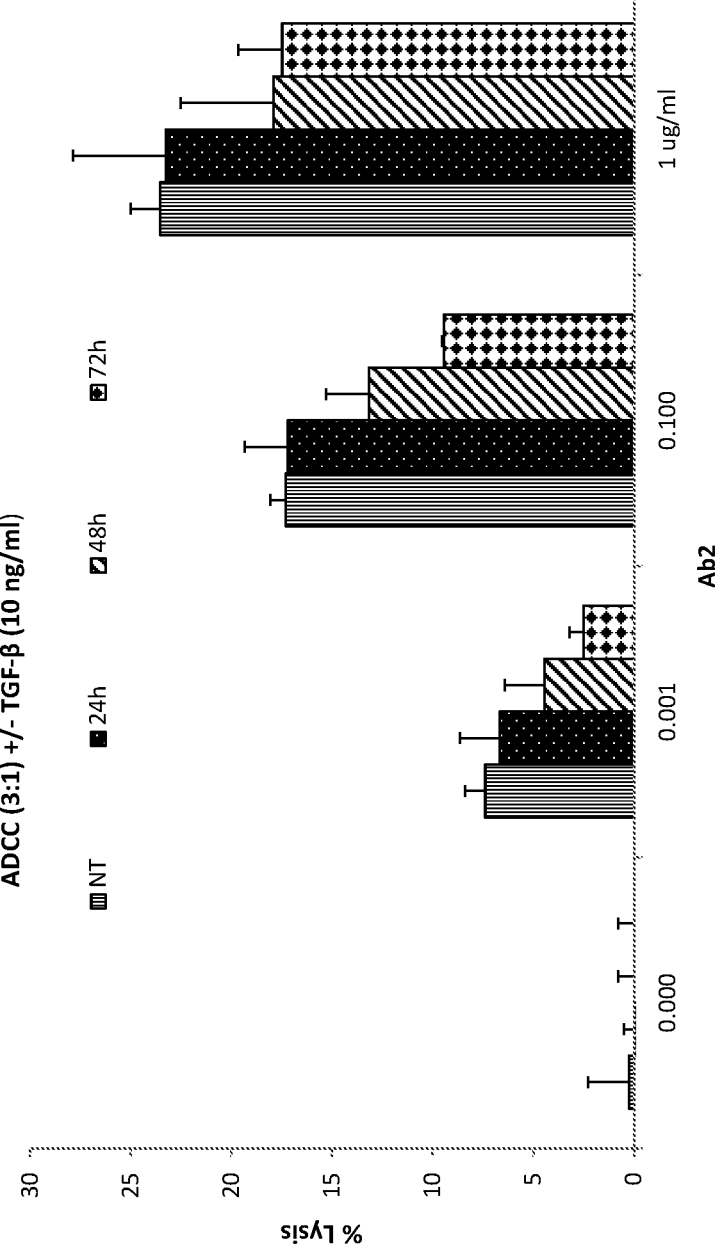
FIG. 2 is a graph showing calcein fluorescence levels (% lysis) from MOLP8 target cells incubated with Ab2 at a concentration of 0, 0.001, 0.1, or 1 µg/mL and lysed for 1 hour by human NK cells incubated with 10 ng/mL TGF-β for overnight, 24 hours, 48 hours, or 72 hours.

Incubation of human NK cells with TGF-β for up to 72 h resulted in a time dependent decrease of Ab2-mediated ADCC (E:T=3:1). While NK cells incubated with TGF-β for 24 h retained their lytic activity, the lysis by NK cells incubated for 48 or 72 h was reduced by approximately 25-60% (FIG. 2).

Example 3: TGF-β Neutralization Restores NK Cytolytic Activity and Ab2-Mediated ADCC Log growth phase NK92V cells (NK92-05 CD16 V/V; Conkwest) were suspended in growth medium (Middle MyeloCult H5100 (Stemcell Technologies cat. no. 05150) supplemented with 100 units/mL human Interleukin-2 (R&D cat. no. 202-IL-010/CF)) and seeded into 10 cm dishes at a density of $0.8\times10^5$ cells per mL. The cells were treated with recombinant human TGF-β at a final concentration of 10 ng/mL, and with 1D11 (the murine surrogate of Ab1) or an antibody isotype control (13C4; data not shown) at a final concentration of 50 µg/mL, for 90 hours at 37° C.

Calcein (AM) (Invitrogen cat. no. C3100MP) labeled MOLP8 target cells and NK92V effector cells were seeded into 96-well plates at a density of $4\times10^4$ target cells (MOLP8) and $1.2\times10^5$ effector cells (NK92V) per well. The cells were treated with Ab2 at 0, 0.001, 0.01, 0.1, or 1 µg/mL, or with an $IgG_1$ control at 1 µg/mL, for 1 hour at 37° C. Released calcein florescence from lysed target cells in the supernatants was measured using a multimode plate reader (Envision). The intensity of the fluorescence signal was directly proportional to the number of lysed target cells.

Figure 3:
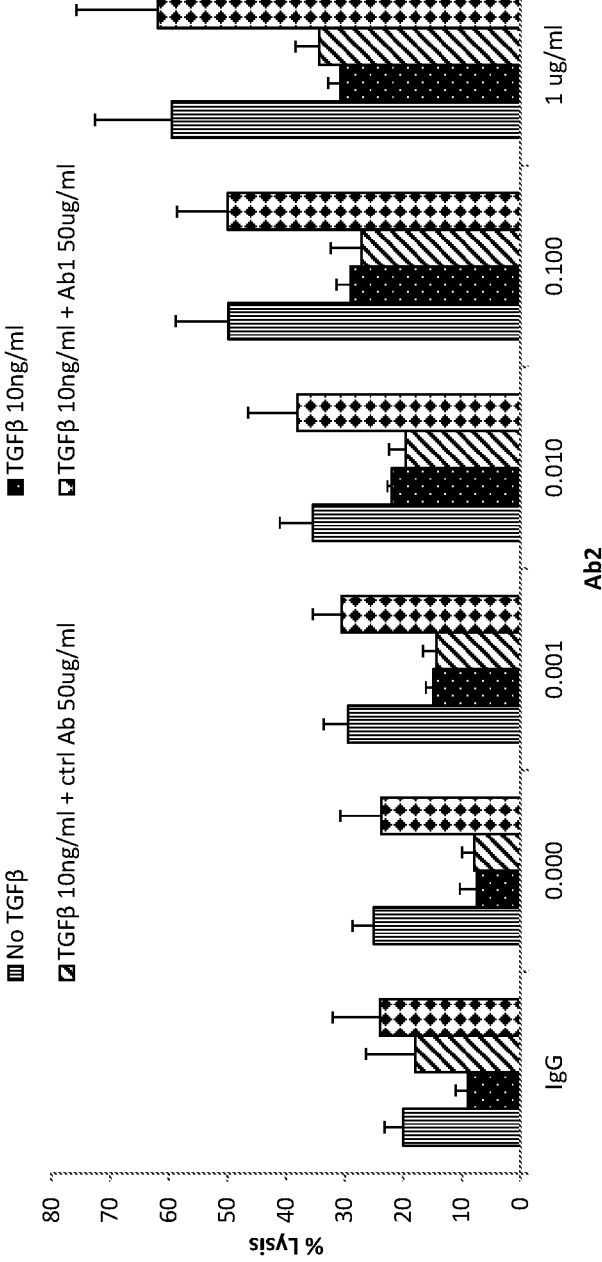
FIG. 3 is a graph showing calcein fluorescence levels (% lysis) from MOLP8 target cells incubated with Ab2 at a concentration of 0, 0.001, 0.01, 0.1, or 1 µg/mL or an IgG$_1$ control and lysed for 1 hour by human NK cells incubated with 10 ng/mL TGF-β and 50 µg/mL Ab1 for 90 hours.

The decrease in the lytic activity of NK cells and Ab2-mediated ADCC induced by TGF-β was fully restored when TGF-β was neutralized by Ab1, but not by a control antibody (FIG. 3).

Figure 4:
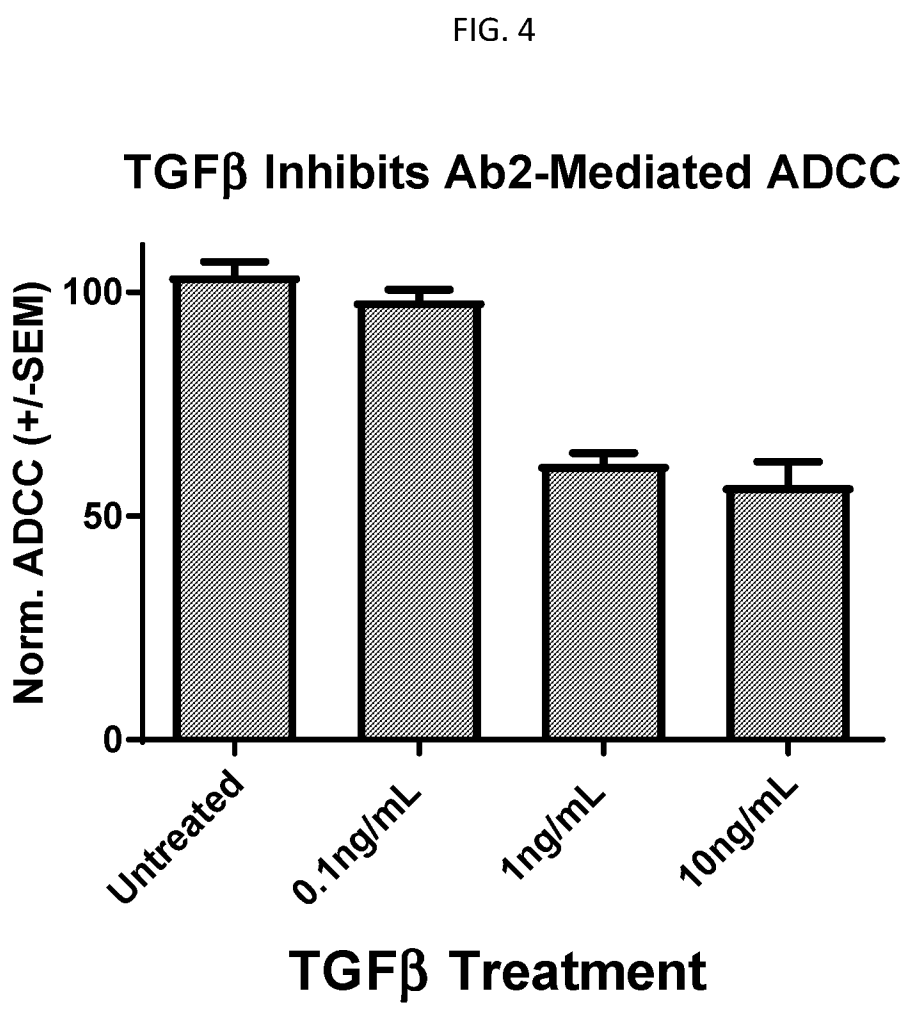
Figure 5:
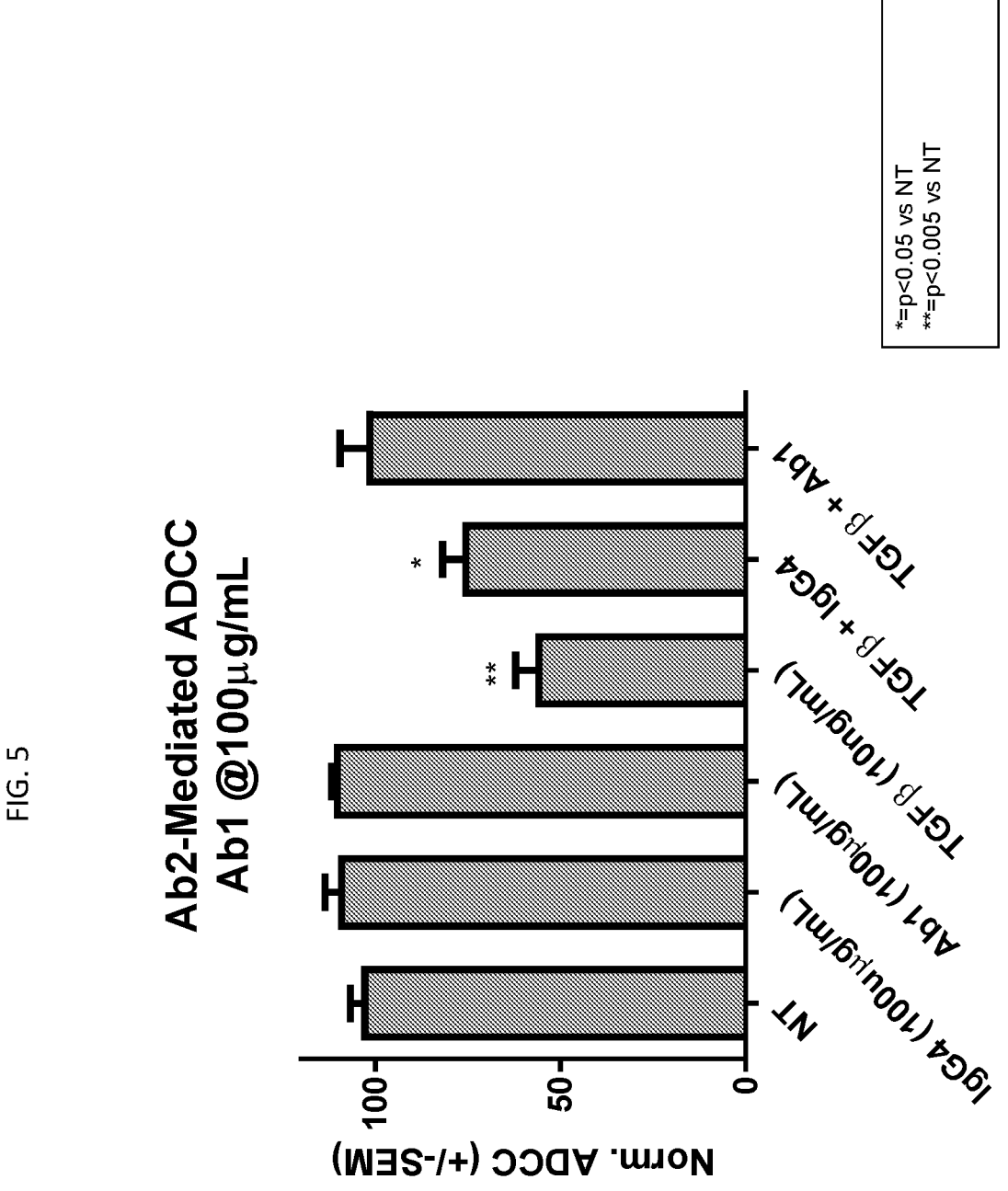
FIG. 5 is a graph showing Ab2-mediated ADCC of NCI-H929 cells treated with 100 µg/mL IgG$_4$, 100 µg/mL Ab1, 10 ng/mL TGF-β, TGF-β+IgG$_4$, or TGF-β+Ab1. *=p<0.05 vs NT; **=p<0.005 vs NT.
Figure 6:
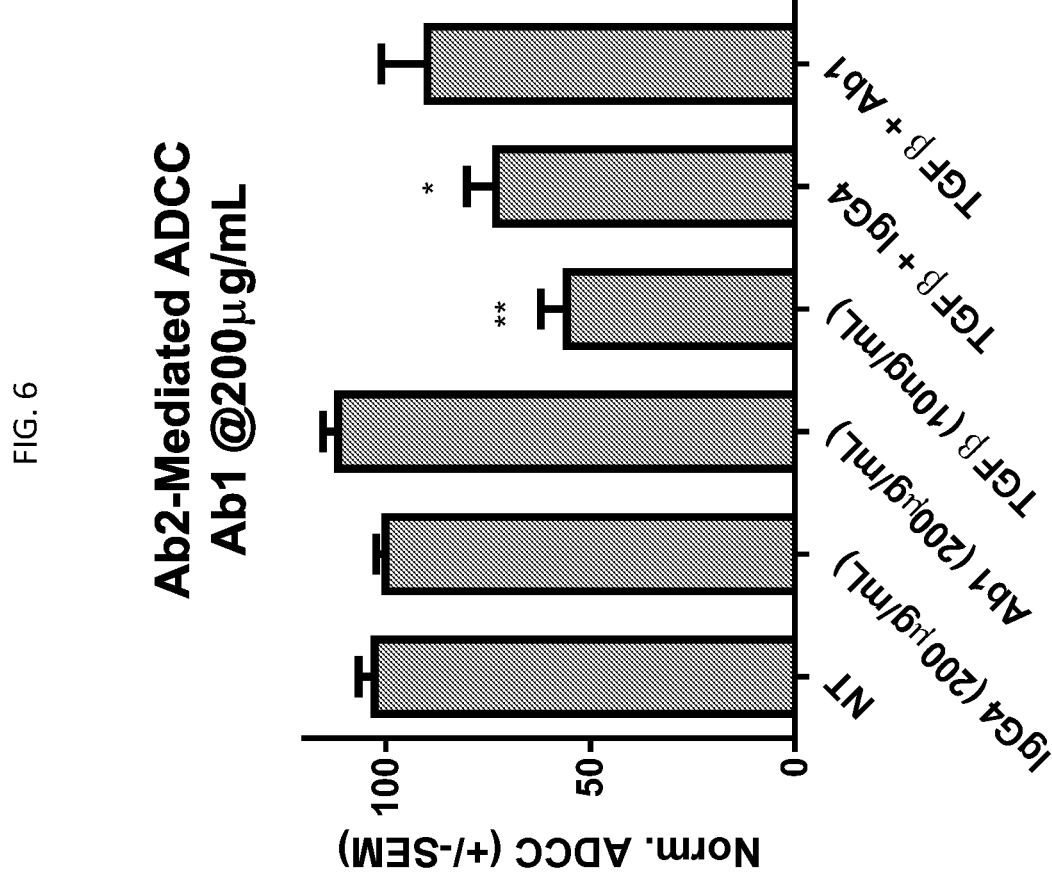
FIG. 6 is a graph showing Ab2-mediated ADCC of NCI-H929 cells treated with 200 µg/mL IgG$_4$, 200 µg/mL Ab1, 10 ng/mL TGF-β, TGF-β+IgG$_4$, or TGF-β+Ab1. *=p<0.05 vs NT; **=p<0.005 vs NT.

Example 4: TGF-β Inhibits Ab2-Mediated ADCC of NCI-H929 Cells and Ab1 Blocks this Inhibition Human NK cells were isolated by negative selection from normal human donors (Stem Cell Technologies). The enriched NK cells were cultured in the presence of IL-2 (at 100 IUs/mL), TGF-β (as indicated) and/or Ab1 or isotype control for 3 days at 37° C. in a humidified incubator. At this point, exponentially growing NCI-H929 cells were labeled with Calcein (AM) and incubated with Ab2 at 1 µg/mL for 30 minutes. The NK effector cells were then resuspended and combined with the labeled target NCI-H929 cells for 1 hour in a humidified incubator. The Ab2-mediated ADCC was quantitated by measuring the levels of target cells labeled with Calcein (AM) using a spectrophotometer. Increasing doses of TGF-β are shown to inhibit the ability of normal human NK cells to kill Ab2-pretreated NCI-H929 cells with 0.1 ng/mL having little effect on the NK cell mediated cell lysis, but 1 and 10 ng/mL blocking the ADCC by approximately 50% (FIG. 4). ADCC was next evaluated at 2 different concentrations of Ab1 (100 and 200 µg/mL). Neither the isotype control Ab ($IgG_4$) or Ab1 had any effect on ADCC when added to the cultures in the absence of TGF-β (FIGS. 5 and 6). Ab1 was shown to block the ability of TGF-β to inhibit ADCC (FIGS. 5 and 6, p<0.005 vs. untreated), while the $IgG_4$ control was unable to block the effects of TGF-β to the same degree. Thus, this data demonstrates that Ab1 is able to relieve the immunosuppressive effects of TGF-β on NK cell-mediated ADCC.

Example 5: Neutralization of Endogenous TGF-β by Ab1 Restores Primary NK Cytolytic Activity and Ab2-Mediated ADCC JJN3, K562, and RPMI8226 cells were cultured in RPMI 1640 (Invitrogen cat. no. 22400-089) supplemented with 10% fetal calf serum (Invitrogen cat. no. 10082-147).

Human primary NK cells were isolated by negative selection from normal human PBMCs according to manufacturer suggested protocols (StemCell Technologies cat. no. 17955RF). The isolated NK cells were either cultured alone or co-cultured in the presence of JJN3 cells in 6-transwell plates in the presence or absence of 100 mg/ml of Ab1 or an isotype control for 90 hours at 37° C. in a 5% $CO_2$ incubator.

After 90 hours of co-culture, NK cells from the transwells were incubated either with K562 cells labeled with Calcein (AM) (Invitrogen cat. no. C3100MP) for 2 hours at 37° C. for NK cell cytolytic function detection, or with Calcein (AM)-labeled RPMI8226 in the presence of 0.001 or 0.1 mg/ml of Ab2, or 0.1 mg/ml of control Ab2 mutant (Ab*) for 1 hour at 37° C. for Ab2-mediated ADCC detection. Released calcein fluorescence from lysed target cells in the supernatants was measured using a multimode plate reader (Envision). The intensity of the fluorescent signal was directly proportional to the number of lysed target cells.

Figure 7:
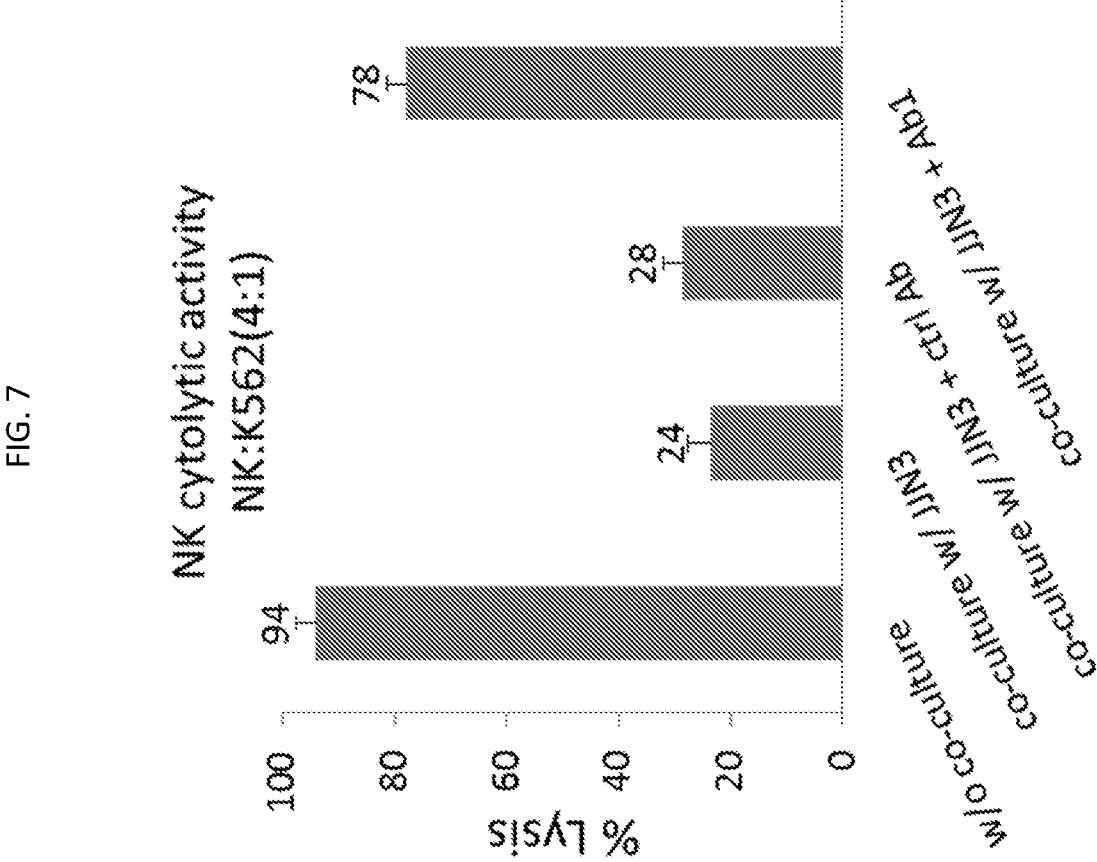
FIG. 7 is a graph showing calcein fluorescence levels (% lysis) from K562 target cells lysed by the cytolytic activity of human NK cells incubated with endogenous TGF-β-releasing JJN3 cells and 100 µg/mL Ab1 or an isotype control for 90 hours.
Figure 8:
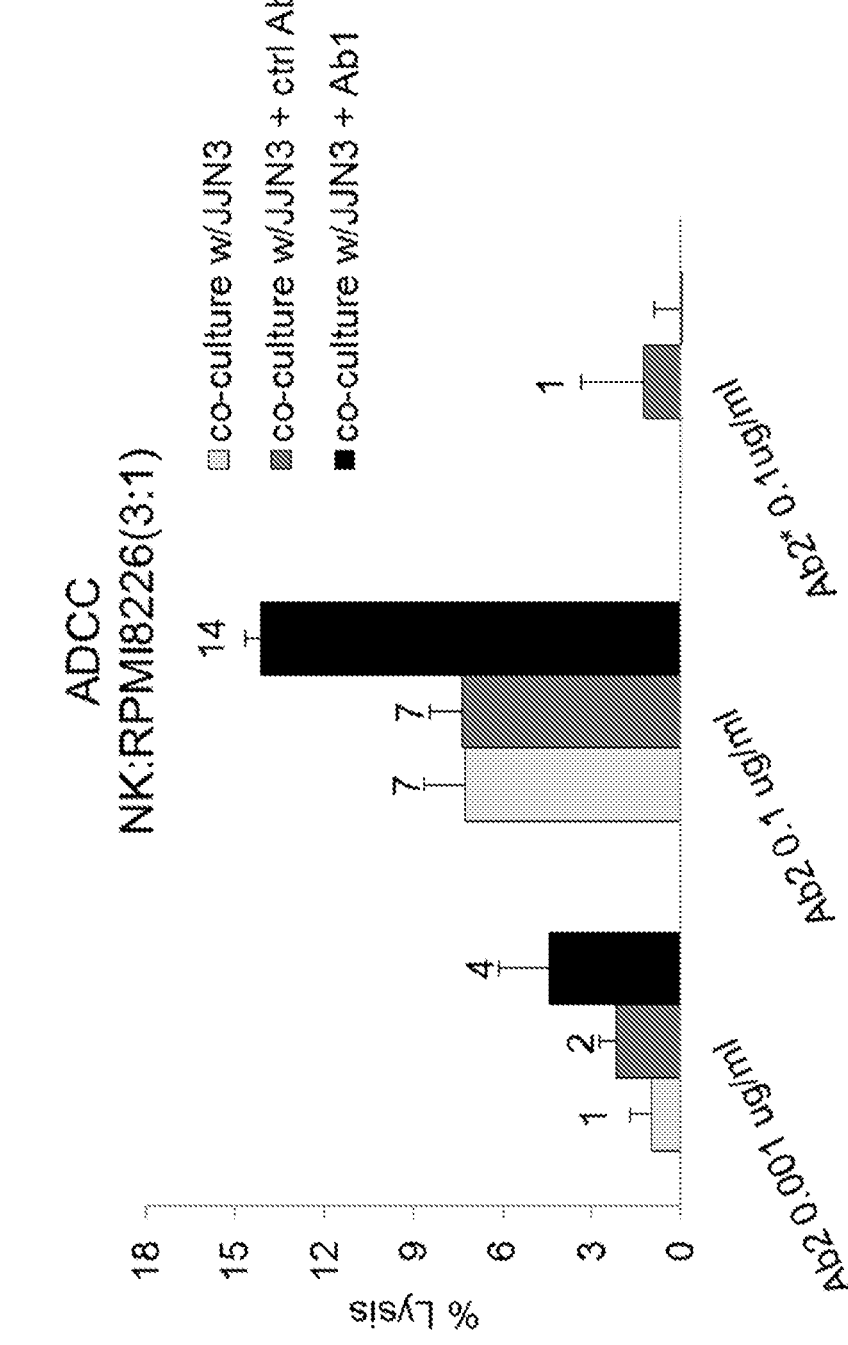
FIG. 8 is a graph showing Ab2-mediated ADCC of RPMI8226 target cells incubated with Ab2 at a concentration of 0, 0.01, or 0.1 µg/mL or with a control Ab2 mutant at a concentration of 0.1 µg/mL and lysed for 1 hour by human NK cells incubated with endogenous TGF-β-releasing JJN3 cells and 100 µg/mL Ab1 or an isotype control for 90 hours.

The increased cytolytic activity of primary NK cells (FIG. 7) and increased Ab2-mediated ADCC (FIG. 8) demonstrate that the presence of Ab1 neutralized JJN3 cell-released endogenous TGFβ during the 90 hour co-culture.

Example 6: Combination Treatment with Ab1 and Ab2 in Multiple Myeloma Patients The effect of combination treatment with antibodies Ab1 and Ab2 may be further assessed in human patients, such as multiple myeloma patients resistant to one or more other treatments targeting CD38 (e.g., isatuximab or daratumumab). The multiple myeloma patients may, for example, be nonresponsive to the other treatment targeting CD38 or have progressed during treatment with the other treatment targeting CD38.

It is expected that the combination of Ab1 and Ab2 will treat multiple myeloma more effectively than Ab2 alone. For example, the combination treatment may result in improved symptoms, reduced bone destruction, enhanced bone formation resulting in bone remodeling and/or bone healing, delayed cancer progression or recurrence, or longer life expectancy in comparison to treatment with Ab2 alone.

Ab1 and Ab2 may be administered at dosages (e.g., 1-20 mg/kg), using dosing schedules (e.g., every one, two, three, or four weeks), and for periods of time necessary to achieve a desired result, e.g., as determined by a physician. In some embodiments, either or both antibodies may be administered via intravenous infusion. In certain embodiments, Ab2 is administered at 10 mg/kg or 16 mg/kg actual body weight every one, two, three, or four weeks, or any combination thereof over the course of treatment.

LIST OF SEQUENCES
(Ab1 heavy chain)

SEQ ID NO: 1

QVQLVQSGAE VKKPGSSVKV SCKASGYTFS SNVISWVRQA PGQGLEWMGG VIPTVDTANY

AQRFKGRVTI TADESTSTTY MELSSLRSED TAVYYCASTL GLVLDAMDYW GQGTLVTVSS

ASTKGPSVFP LAPCSRSTSE STAALGCLVK DYFPEPVTVS WNSGALTSGV HTFPAVLQSS

GLYSLSSVVT VPSSSLGTKT YTCNVDHKPS NTKVDKRVES KYGPPCPPCP APEFLGGPSV

FLFPPKPKDT LMISRTPEVT CVVVDVSQED PEVQFNWYVD GVEVHNAKTK PREEQFNSTY

RVVSVLTVLH QDWLNGKEYK CKVSNKGLPS STEKTISKAK GQPREPQVYT LPPSQEEMTK

NQVSLTCLVK GFYPSDIAVE WESNGQPENN YKTTPPVLDS DGSFFLYSRL TVDKSRWQEG

NVFSCSVMHE ALHNHYTQKS LSLSLGK (Ab1 light chain)

SEQ ID NO: 2

ETVLTQSPGT LSLSPGERAT LSCRASQSLG SSYLAWYQQK PGQAPRLLTY GASSRAPGIP

DRFSGSGSGT DFTLTISRLE PEDFAVYYCQ QYADSPITFG QGTRLETKRT VAAPSVFIFP

PSDEQLKSGT ASVVCLLNNF YPREAKVQWK VDNALQSGNS QESVTEQDSK DSTYSLSSTL

TLSKADYEKH KVYACEVTHQ GLSSPVTKSF NRGEC (Ab1 heavy chain variable domain)

SEQ ID NO: 3

QVQLVQSGAE VKKPGSSVKV SCKASGYTFS SNVISWVRQA PGQGLEWMGG VIPTVDTANY

AQRFKGRVTI TADESTSTTY MELSSLRSED TAVYYCASTL GLVLDAMDYW GQGTLVTVSS (Ab1 light chain variable domain)

SEQ ID NO: 4

ETVLTQSPGT LSLSPGERAT LSCRASQSLG SSYLAWYQQK PGQAPRLLTY GASSRAPGIP

DRFSGSGSGT DFTLTISRLE PEDFAVYYCQ QYADSPITFG QGTRLEIK (Ab1 heavy chain CDR1)

SEQ ID NO: 5

SNVIS (Ab1 heavy chain CDR2)

SEQ ID NO: 6

GVIPTVDTAN Y (Ab1 heavy chain CDR3)

SEQ ID NO: 7

TLGLVLDAMD Y (Ab1 light chain CDR1)

SEQ ID NO: 8

RASQSLGSSY LA (Ab1 light chain CDR2)

SEQ ID NO: 9

GASSRAP (Ab1 light chain CDR3)

SEQ ID NO: 10

QQYADSPIT (Ab2 heavy chain)

SEQ ID NO: 11

QVQLVQSGAE VAKPGTSVKL SCKASGYTFT DYWMQWVKQR PGQGLEWIGT IYPGDGDTGY

AQKFQGKATL TADKSSKTVY MHLSSLASED SAVYYCARGD YYGSNSLDYW GQGTSVTVSS

ASTKGPSVFP LAPSSKSTSG GTAALGCLVK DYFPEPVTVS WNSGALTSGV HTFPAVLQSS

GLYSLSSVVT VPSSSLGTQT YICNVNHKPS NTKVDKKVEP KSCDKTHTCP PCPAPELLGG

PSVFLFPPKP KDTLMISRTP EVTCVVVDVS HEDPEVKFNW YVDGVEVHNA KTKPREEQYN

-continued

STYRVVSVLT VLHQDWLNGK EYKCKVSNKA LPAPIEKTIS KAKGQPREPQ VYTLPPSRDE

LTKNQVSLTC LVKGFYPSDI AVEWESNGQP ENNYKTTPPV LDSDGSFFLY SKLTVDKSRW

QQGNVFSCSV MHEALHNHYT QKSLSLSPGK (Ab2 light chain)

SEQ ID NO: 12

DIVMTQSHLS MSTSLGDPVS ITCKASQDVS TVVAWYQQKP GQSPRRLIYS ASYRYIGVPD

RFTGSGAGTD FTFTISSVQA EDLAVYYCQQ HYSPPYTFGG GTKLEIKRTV AAPSVFIFPP

SDEQLKSGTA SVVCLLNNFY PREAKVQWKV DNALQSGNSQ ESVTEQDSKD STYSLSSTLT

LSKADYEKHK VYACEVTHQG LSSPVTKSFN RGEC (Ab2 heavy chain variable domain)

SEQ ID NO: 13

QVQLVQSGAE VAKPGTSVKL SCKASGYTFT DYWMQWVKQR PGQGLEWIGT IYPGDGDTGY

AQKFQGKATL TADKSSKTVY MHLSSLASED SAVYYCARGD YYGSNSLDYW GQGTSVTVSS (Ab2 light chain variable domain)

SEQ ID NO: 14

DIVMTQSHLS MSTSLGDPVS ITCKASQDVS TVVAWYQQKP GQSPRRLIYS ASYRYIGVPD

RFTGSGAGTD FTFTISSVQA EDLAVYYCQQ HYSPPYTFGG GTKLEIK (Ab2 heavy chain CDR1)

SEQ ID NO: 15

DYWMQ (Ab2 heavy chain CDR2)

SEQ ID NO: 16

TTYPGDGDTG YAQKFQG (Ab2 heavy chain CDR3)

SEQ ID NO: 17

GDYYGSNSLD Y (Ab2 light chain CDR1)

SEQ ID NO: 18

KASQDVSTVV A (Ab2 light chain CDR2)

SEQ ID NO: 19

SASYRYI (Ab2 light chain CDR3)

SEQ ID NO: 20

QQHYSPPYT (human TGF-β1): SwissProt P01137

SEQ ID NO: 21

MPPSGLRLLL LLLPLLWLLV LTPGRPAAGL STCKTIDMEL VKRKRIEAIR GQILSKLRLA

SPPSQGEVPP GPLPEAVLAL YNSTRDRVAG ESAEPEPEPE ADYYAKEVTR VLMVETHNET

YDKFKQSTHS TYMFFNTSEL REAVPEPVLL SRAELRLLRL KLKVEQHVEL YQKYSNNSWR

YLSNRLLAPS DSPEWLSFDV TGVVRQWLSR GGETEGFRLS AHCSCDSRDN TLQVDINGFT

TGRRGDLATI HGMNRPFLLL MATPLERAQH LQSSRHRRAL DTNYCFSSTE KNCCVRQLYI

DFRKDLGWKW THEPKGYHAN FCLGPCPYTW SLDTQYSKVL ALYNQHNPGA SAAPCCVPQA

LEPLPIVYYV GRKPKVEQLS NMIVRSCKCS (human TGF-β2): SwissProt P08112

SEQ ID NO: 22

MHYCVLSAFL ILHLVTVALS LSTCSTLDMD QFMRKRIEAT RGQILSKLKL TSPPEDYPEP

EEVPPEVIST YNSTRDLLQE KASRRAAACE RERSDEEYYA KEVYKIDMPP FFPSENAIPP

TFYRPYFRIV RFDVSAMEKN ASNLVKAEFR VFRLQNPKAR VPEQRTELYQ ILKSKDLTSP

TQRYIDSKVV KTRAEGEWLS FDVTDAVHEW LHHKDRNLGF KISLHCPCCT FVPSNNYTIP

NKSEELEARF AGIDGTSTYT SGDQKTIKST RKKNSGKTPH LLLMLLPSYR LESQQTNRRK

-continued

```
KRALDAAYCF RNVQDNCCLR PLYIDFKRDL GWKWIHEPKG YNANFCAGAC PYLWSSDTQH

SRVLSLYNTI NPEASASPCC VSQDLEPLTI LYYIGKTPKI EQLSNMIVKS CKCS
```

(human TGF-β3): SwissProt P10600

SEQ ID NO: 23
```
MKMHLQRALV VLALLNFATV SLSLSTCTTL DFGHIKKKRV EAIRGQILSK LRLTSPPEPT

VMTHVPYQVL ALYNSTRELL EEMHGEREEG CTQENTESEY YAKEIHKFDM IQGLAEHNEL

AVCPKGITSK VFRFNVSSVE KNRTNLFRAE FRVLRVPNPS SKRNEQRIEL FQILRPDEHI

AKQRYIGGKN LPTRGTAEWL SFDVTDTVRE WLLRRESNLG LEISIHCPCH TFQPNGDILE

NIHEVMEIKF KGVDNEDDHG RGDLGRLKKQ KDHHNPHLIL MMIPPHRLDN PGQGGQRKKR

ALDTNYCFRN LEENCCVRPL YIDFRQDLGW KWVHEPKGYY ANFCSGPCPY LRSADTTHST

VLGLYNTLNP EASASPCCVP QDLEPLTILY YVGRTPKVEQ LSNMVVKSCK CS
```

(human CD38): GenBank NP_001766

SEQ ID NO: 24
```
MANCEFSPVS GDKPCCRLSR RAQLCLGVSI LVLILVVVLA VVVPRWRQQW SGPGTTKRFP

ETVLARCVKY TEIHPEMRHV DCQSVWDAFK GAFISKHPCN ITEEDYQPLM KLGTQTVPCN

KILLWSRIKD LAHQFTQVQR DMFTLEDTLL GYLADDLTWC GEFNTSKINY QSCPDWRKDC

SNNPVSVFWK TVSRRFAEAA CDVVHVMLNG SRSKIFDKNS TFGSVEVHNL QPEKVQTLEA

WVIHGGREDS RDLCQDPTIK ELESIISKRN IQFSCKNIYR PDKFLQCVKN PEDSSCTSEI
```

(Ab3 heavy chain)

SEQ ID NO: 25
```
QVQLVQSGAE VVKPGASVKV SCKASGYTFT SYAMHWVKEA PGQRLEWIGY IYPGQGGTNY

NQKFQGRATL TADTSASTAY MELSSLRSED TAVYFCARTG GLRRAYFTYW GQGTLVTVSS

ASTKGPSVFP LAPSSKSTSG GTAALGCLVK DYFPEPVTVS WNSGALTSGV HTFPAVLQSS

GLYSLSSVVT VPSSSLGTQT YICNVNHKPS NTKVDKKVEP KSCDKTHTCP PCPAPELLAG

PDVFLFPPKP KDTLMISRTP EVTCVVVDVS HEDPEVKFNW YVDGVEVHNA KTKPREEQYN

STYRVVSVLT VLHQDWLNGK EYKCKVSNKA LPLPEEKTIS KAKGQPREPQ VYTLPPSRDE

LTKNQVSLTC LVKGFYPSDI AVEWESNGQP ENNYKTTPPV LDSDGSFFLY SKLTVDKSRW

QQGNVFSCSV MHEALHNHYT QKSLSLSPG
```

(Ab3 light chain)

SEQ ID NO: 26
```
DIVLTQSPAT LSLSPGERAT ISCRASQSVS SYGQGFMHWY QQKPGQPPRL LIYGASSRAT

GIPARFSGSG SGTDFTLTIS PLEPEDFAVY YCQQNKEDPW TFGGGTKLEI KRTVAAPSVF

IFPPSDEQLK SGTASVVCLL NNFYPREAKV QWKVDNALQS GNSQESVTEQ DSKDSTYSLS

STLTLSKADY EKHKVYACEV THQGLSSPVT KSFNRGEC
```

(Ab3 heavy chain variable domain)

SEQ ID NO: 27
```
QVQLVQSGAE VVKPGASVKV SCKASGYTFT SYAMHWVKEA PGQRLEWIGY IYPGQGGTNY

NQKFQGRATL TADTSASTAY MELSSLRSED TAVYFCARTG GLRRAYFTYW GQGTLVTVSS
```

(Ab3 light chain variable domain)

SEQ ID NO: 28
```
DIVLTQSPAT LSLSPGERAT ISCRASQSVS SYGQGFMHWY QQKPGQPPRL LIYGASSRAT

GIPARFSGSG SGTDFTLTIS PLEPEDFAVY YCQQNKEDPW TFGGGTKLEI K
```

(Ab3 heavy chain CDR1)

SEQ ID NO: 29
```
GYTFTSYA
```

(Ab3 heavy chain CDR2)

SEQ ID NO: 30
```
IYPGQGGT
```

-continued (Ab3 heavy chain CDR3)
                                                    SEQ ID NO: 31
ARTGGLRRAY FTY (Ab3 light chain CDR1)
                                                    SEQ ID NO: 32
QSVSSYGQGF (Ab3 light chain CDR2)
                                                    SEQ ID NO: 33
GAS (Ab3 light chain CDR3)
                                                    SEQ ID NO: 34
QQNKED PWT (Ab4 heavy chain)
                                                    SEQ ID NO: 35
QVQLVESGGG VVQPGRSLRL SCAASGFTFS SYGMHWVRQA PGKGLEWVAV IWYDGSNKYY

ADSVKGRFTI SGDNSKNTLY LQMNSLRAED TAVYYCARMF RGAFDYWGQG TLVTVSSAST

KGPSVFPLAP SSKSTSGGTA ALGCLVKDYF PEPVTVSWNS GALTSGVHTF PAVLQSSGLY

SLSSVVTVPS SSLGTQTYIC NVNHKPSNTK VDKKVEPKSC DKTHTCPPCP APELLAGPDV

FLFPPKPKDT LMISRTPEVT CVVVDVSHED PEVKFNWYVD GVEVHNAKTK PREEQYNSTY

RVVSVLTVLH QDWLNGKEYK CKVSNKALPL PEEKTISKAK GQPREPQVYT LPPSRDELTK

NQVSLTCLVK GFYPSDIAVE WESNGQPENN YKTTPPVLDS DGSFFLYSKL TVDKSRWQQG

NVFSCSVMHE ALHNHYTQKS LSLSPG (Ab4 light chain)
                                                    SEQ ID NO: 36
AIQMTQSPSS LSASVGDRVT ITCRASQGIR NDLGWYQQKP GKAPKLLIYA ASSLQSGVPS

RFSGSGSGTD FTLTISGLQP EDSATYYCLQ DYIYYPTFGQ GTKVEIKRTV AAPSVFIFPP

SDEQLKSGTA SVVCLLNNFY PREAKVQWKV DNALQSGNSQ ESVTEQDSKD STYSLSSTLT

LSKADYEKHK VYACEVTHQG LSSPVTKSFN RGEC (Ab4 heavy chain variable domain)
                                                    SEQ ID NO: 37
QVQLVESGGG VVQPGRSLRL SCAASGFTFS SYGMHWVRQA PGKGLEWVAV IWYDGSNKYY

ADSVKGRFTI SGDNSKNTLY LQMNSLRAED TAVYYCARMF RGAFDYWGQG TLVTVSS (Ab4 light chain variable domain)
                                                    SEQ ID NO: 38
AIQMTQSPSS LSASVGDRVT ITCRASQGIR NDLGWYQQKP GKAPKLLIYA ASSLQSGVPS

RFSGSGSGTD FTLTISGLQP EDSATYYCLQ DYIYYPTFGQ GTKVEIK (Ab4 heavy chain CDR1)
                                                    SEQ ID NO: 39
GFTFSSYG (Ab4 heavy chain CDR2)
                                                    SEQ ID NO: 40
IWYDGSNK (Ab4 heavy chain CDR3)
                                                    SEQ ID NO: 41
ARMFRGAFDY (Ab4 light chain CDR1)
                                                    SEQ ID NO: 42
QGIRND (Ab4 light chain CDR2)
                                                    SEQ ID NO: 43
AAS (Ab4 light chain CDR3)
                                                    SEQ ID NO: 44
LQDYIYYPT

What is claimed is:

1. A method of treating a CD38-positive cancer in a human patient in need thereof, comprising administering to the patient an anti-CD38 antibody that has heavy chain CDR1 (HCDR1), HCDR2, HCDR3, light chain CDR1 (LCDR1), LCDR2, and LCDR3 comprising the amino acid sequences of SEQ ID NOs: 15-20, respectively, and an anti-TGF-β antibody or an antigen-binding fragment thereof that has HCDR1, HCDR2, HCDR3, LCDR1, LCDR2, and LCDR3 comprising the amino acid sequences of SEQ ID NOs: 5-10, respectively, wherein the cancer is multiple myeloma that is refractory to treatment with Ab2, and the administering of the anti-CD38 antibody and the anti-TGF-β antibody or antigen-binding fragment slows cancer growth.

2. The method of claim 1, wherein the anti-CD38 antibody comprises a heavy chain variable domain ($V_H$) and a light chain variable domain ($V_L$) comprising the amino acid sequences of SEQ ID NOs: 13 and 14, respectively; and wherein the anti-TGF-β antibody comprises a $V_H$ and a $V_L$ comprising the amino acid sequences of SEQ ID NOs: 3 and 4, respectively.

3. The method of claim 2, wherein the anti-CD38 antibody has a heavy chain (HC) and a light chain (LC) comprising the amino acid sequences of SEQ ID NOs: 11 and 12, respectively; and wherein the anti-TGF-β antibody has an HC and an LC comprising the amino acid sequences of SEQ ID NOs: 1 and 2, respectively.

4. A method of treating a CD38-positive cancer in a human patient in need thereof, comprising administering to the patient an anti-CD38 antibody and an anti-TGF-β antibody or an antigen-binding fragment thereof, wherein the anti-CD38 antibody:

a) has HCDR1-3 and LCDR1-3 comprising the amino acid sequences of SEQ ID NOs: 15-20, respectively;

b) has a heavy chain variable domain ($V_H$) and a light chain variable domain ($V_L$) comprising the amino acid sequences of SEQ ID NOs: 13 and 14, respectively; or c) has a heavy chain (HC) and a light chain (LC) comprising the amino acid sequences of SEQ ID NOs: 11 and 12, respectively; and wherein the anti-TGF-β antibody:

a) has HCDR1-3 and LCDR1-3 comprising the amino acid sequences of SEQ ID NOs: 5-10, respectively;

b) has a $V_H$ and a $V_L$ comprising the amino acid sequences of SEQ ID NOs: 3 and 4, respectively; or c) has an HC and an LC comprising the amino acid sequences of SEQ ID NOs: 1 and 2, respectively, wherein the cancer is multiple myeloma that is refractory to treatment with Ab2, and the administering of the anti-CD38 antibody and the anti-TGF-β antibody or antigen-binding fragment slows cancer growth.

5. The method of claim 1, wherein the anti-CD38 antibody comprises a human $IgG_1$ Fc region and the anti-TGF-β antibody comprises a human $IgG_4$ Fc region.

6. A method of treating multiple myeloma in a human patient in need thereof, comprising administering to the patient an anti-CD38 antibody that comprises a heavy chain variable domain ($V_H$) amino acid sequence of SEQ ID NO: 13 and a light chain variable domain ($V_L$) amino acid sequence of SEQ ID NO: 14, and an anti-TGF-β antibody that comprises a $V_H$ amino acid sequence of SEQ ID NO: 3 and a $V_L$ amino acid sequence of SEQ ID NO: 4, wherein the cancer is multiple myeloma that is refractory to treatment with Ab2, and the administering of the anti-CD38 antibody and the anti-TGF-β antibody or antigen-binding fragment slows cancer growth.

7. A method of treating multiple myeloma in a human patient in need thereof, comprising administering to the patient an anti-CD38 antibody that comprises a heavy chain (HC) amino acid sequence of SEQ ID NO: 11 and a light chain (LC) amino acid sequence of SEQ ID NO: 12, and an anti-TGF-β antibody that comprises an HC amino acid sequence of SEQ ID NO: 1 and an LC amino acid sequence of SEQ ID NO: 2, wherein the cancer is multiple myeloma that is refractory to treatment with Ab2, and the administering of the anti-CD38 antibody and the anti-TGF-β antibody or antigen-binding fragment slows cancer growth.

8. The method of claim 1, wherein the anti-CD38 antibody and the anti-TGF-β antibody or fragment are administered to the patient sequentially.

9. The method of claim 1, wherein the treatment results in less bone destruction than treatment with the anti-CD38 antibody alone.

10. The method of claim 1, wherein the treatment enhances bone healing.

11. The method of claim 1, wherein the treatment further comprises dexamethasone.

* * * * *